(12) United States Patent
Meglen et al.

(10) Patent No.: US 6,525,319 B2
(45) Date of Patent: Feb. 25, 2003

(54) USE OF A REGION OF THE VISIBLE AND NEAR INFRARED SPECTRUM TO PREDICT MECHANICAL PROPERTIES OF WET WOOD AND STANDING TREES

(75) Inventors: Robert R. Meglen, Boulder, CO (US); Stephen S. Kelley, Evergreen, CO (US)

(73) Assignee: Midwest Research Institute, Kansas City, MO (US)

( * ) Notice: Subject to any disclaimer, the term of this patent is extended or adjusted under 35 U.S.C. 154(b) by 31 days.

(21) Appl. No.: 09/740,293

(22) Filed: Dec. 15, 2000

(65) Prior Publication Data

US 2002/0113212 A1 Aug. 22, 2002

(51) Int. Cl.$^7$ .............................................. G01N 21/00
(52) U.S. Cl. .............................. 250/339.05; 250/339.07
(58) Field of Search ...................... 250/339.05, 339.07, 250/339.09, 339.11, 358.1; 356/432, 632

(56) References Cited

U.S. PATENT DOCUMENTS

| | | | |
|---|---|---|---|
| 4,606,645 A | * 8/1986 | Matthews et al. | 356/446 |
| 4,885,709 A | * 12/1989 | Edgar et al. | 364/563 |
| 5,536,942 A | 7/1996 | Barringer et al. | 250/339.12 |
| 5,638,284 A | 6/1997 | Helmer et al. | 364/498 |
| 5,680,320 A | 10/1997 | Helmer et al. | 364/498 |
| 5,680,321 A | 10/1997 | Helmer et al. | 364/499 |
| 5,945,676 A | 8/1999 | Khalil et al. | 250/339.12 |
| 5,965,888 A | 10/1999 | Engstrom et al. | 250/339.09 |
| 6,031,233 A | 2/2000 | Levin et al. | 250/339.11 |
| 2001/0028459 A1 | * 10/2001 | Hartenstein et al. | 356/429 |

OTHER PUBLICATIONS

Brown, S.D., "Chemometrics", Anal. Chem. 62, 84R–101R (1990).

Hoffmeyer, P., et al., Holz als Roh–und Werkstoff 53 (1995) 165–170 (Density and Strength from a Dry Sample).

* cited by examiner

*Primary Examiner*—Constantine Hannaher
*Assistant Examiner*—Otilia Gabor
(74) *Attorney, Agent, or Firm*—Paul J. White

(57) ABSTRACT

In a method for determining the dry mechanical strength for a green wood, the improvement comprising: (a) illuminating a surface of the wood to be determined with a reduced range of wavelengths in the VIS-NIR spectra 400 to 1150 nm, said wood having a green moisture content; (b) analyzing the surface of the wood using a spectrometric method, the method generating a first spectral data of a reduced range of wavelengths in VIS-NIR spectra; and (c) using a multivariate analysis technique to predict the mechanical strength of green wood when dry by comparing the first spectral data with a calibration model, the calibration model comprising a second spectrometric method of spectral data of a reduced range of wavelengths in VIS-NIR spectra obtained from a reference wood having a green moisture content, the second spectral being correlated with a known mechanical strength analytical result obtained from the reference wood when dried and a having a dry moisture content.

34 Claims, 30 Drawing Sheets

USE OF A REGION OF THE VISIBLE AND NEAR INFRARED SPECTRUM TO PREDICT MECHANICAL PROPERTIES OF WET WOOD AND STANDING TREES

CONTRACTUAL ORIGIN OF THE INVENTION

The United States Government has rights in this invention pursuant to Contract No. DE-AC36-99GO10337 between the United States Department of Energy and the Midwest Research Institute.

BACKGROUND OF THE INVENTION

1. Field of the Invention

This invention relates to the spectral analysis of wood, and in particular to a method for predicting dry mechanical strength properties from the visible region of near infrared (NIR) spectra of green wood using a multivariate calibrations model, and is a continuation-in-part of U.S. patent application Ser. No. 09/738,912 filed Dec. 13, 2000, and entitled Method For Predicting Dry Mechanical Properties of Wet Wood and Standing Trees.

2. Description of the Prior Art

A method for the nondestructive analysis of the quality of a tree, unlike conventional methods, which measure the volume and form of a tree, would provide important information to assist woodland owners in making their thinning decisions, and in the valuation of a stand of timber. The method would also be useful in the analysis of trees or sawn logs, in the woods, for the field sorting of logs to be used as poles, or feedstocks in the manufacture of veneers, lumber or chips.

Visible and near infrared spectroscopy (VIS-NIR) in combination with multivariate data analysis is currently in use for the characterization of complex systems. These several statistical methods are also termed chemometric methods, forming the discipline of chemometrics, when applied generally to the field of chemistry, and in particular to the field of analytical chemistry. The technique of chemometrics is more fully explained in Brown, S. D., "Chemometics", Anal. Chem. 62, 84R-101R (1990).

Near infrared spectroscopy and chemometrics have been described for use in the non-destructive analysis of the chemical and physical properties of paper.

For example, U.S. Pat. No. 5,638,284 describes a method for the measurement of the wet strength of paper by analyzing the visible, near-infrared and/or infrared spectrum of the paper/pulp in the process line using a wavelength range within 400 nm to 4,000 nm, and applying a chemometric evaluation of the spectrum, to calculate the wet strength of the paper. Other examples include U.S. Pat. No. 5,680,321 (determining physical properties selected from dry tensile strength, hydrophobicity, debonding energy, bursting strength, wettability and printability in paper), and U.S. Pat. No. 5,680,320 (quantifying the amounts of reacted and/or retained chemical additives in paper by analysis of the visible, near-infrared and/or infrared spectrum of the paper/pulp in a process line).

While the foregoing art discloses the use of chemometric evaluation in the analysis of paper products, the entire VIS-NIR spectral range between 400 nm and 4,000 nm is used for the evaluation. Also, the mechanical properties of wet-solid-wood samples are much more complex than those of paper due, in part, due to the presence of high concentrations of hemicellulose and lignin in wood relative to these components in paper. The structure and macromolecular morphology of the sample, such as roughness, color, and grain orientation also affect the spectral properties of solid wood. For a wet wood sample, the analysis of these properties is problematic because moisture in the samples, along with the high concentrations of lignin and hemicellulose tends to block or conceal the spectrometric derived information. Furthermore, many of these paper properties are a direct result of the presence of a small amount of an additive, or size or wet-strength resin, rather than a function of the inherent properties of paper fibers.

One example of the VIS-NIR characterization of wood is described in U.S. Pat. No. 5,965,888, in which, NIR spectrometric data are obtained from dried wood chips. The method for the determination of parameters of wood panels comprises analyzing the raw wood chips/panels at a moisture content <10% by a spectrometric method to provide spectral data, and comparing the spectral data with reference spectral data from a reference chip/panel calibrated to known parameters of panels produced from the reference material, or of the reference panel by multivariate analysis. Again this method relies on the entire spectral range between 180 and 2,500 nm. This method is useful in predicting the quality of a dry wood panel based on an analysis of dried wood chips which are used as a feedstock in the manufacturing process.

VIS-NIR has also been used for determination of surface roughness and fiber angle of dry wood relative to the duration of the incident light, and for the evaluation of density and the strength of wood from a dry sample. See, e.g., Hoffmeyer, P., et al., *Holz als Roh-und Werkstoff* 53 (1995) 165–170 (density and strength from a dry sample).

In both U.S. Pat. No. 5,965,888 and Hoffmeyer, P., et al., *Holz als Roh-und Werkstoff* 53 (1995) 165–170, reference is explicitly made to the problems associated with measuring the NIR properties of wet wood, and seek to overcome them with use of a dry sample for analysis. All of these references use the full VIS-NIR spectral range, generally considered to be between 400 and 2,500 nm. Thus, they are using information from more than 2,000 individual wavelengths.

However, none of the foregoing references enables prediction of the dry mechanical strength of wet woody biomass, wood fibers, and various composite materials through the use of VIS-NIR measurements of wet wood coupled with a multivariate statistical calibration model (obtained from data derived from wet spectra together with known dry mechanical strength analytical results input into a computer, and either measuring a plot of modulus of elasticity (MOE) or modulus of rupture (MOR) of the known dry wood regressed against the MOE or MOR predicted by a multivariate model constructed with NIR spectra taken from the wet wood).

U.S. Pat. No. 5,945,676 discloses a method and apparatus for multi-spectral analysis in non-invasive VIS-NIR spectroscopy in which incident radiation containing a plurality of distinct, non-overlapping spectral regions of wavelengths is used to irradiate the sample. Diffusively reflected radiation emerging from the sample is detected, and a value indicative of the concentration of the analyte is obtained, preferably using an application of chemometric techniques.

A hand held device for infra red reflectance measurements of samples to identify the sample material and comprising a self-contained portable unit built into a hand held housing is disclosed in U.S. Pat. No. 6,031,233. The housing includes a window and optics on a bench adjacent the window, so that the optics are aligned with the sample when the device is placed directly against the sample. The optics include a broad-band IR light source shining onto an acousto-optic tunable filter (AOTF), which passes narrow-band IR light with a swept frequency; a lens focusing the IR through the window onto the sample; and a reflectance detector aligned with the window of the housing to pick up reflected light. A computer, which may be mounted in the housing, compares the detected reflectance spectrum with stored sample data spectra, and identifies the material or the components of the material and their proportions.

A need therefore exists to ascertain any advantages of VIS-NIR spectral sensitivity to simultaneously measure density, moisture content, slope in grain, microfibril angle, and other wood features, which when coupled with multivariate statistical analysis, will correlate the subtle spectral differences between wet wood samples to predict dry wood mechanical properties, such as ultimate bending strength or MOR and MOE.

There is a further need to utilize VIS-NIR from a reduced range of wavelengths to enable use of lightweight portable instrument means extensively available in the market to facilitate "on the spot" or swift analysis of NIR spectra for predicting dry mechanical strength from standing trees or wet wood.

There is a need still further to provide a method for determining dry mechanical strength from standing trees or wet wood by the use of low-cost, light weight, spectrometers with vary rapid acquisition times through the use of spectrometers that are commercially available for both in-plant and in-field measurements, due to the fact that in-plant measurements require very rapid spectral acquisition times between 10 microseconds and 1 second, or more, for effective process monitoring, and in view of the fact that many spectrometers require moving parts and mechanical gratings which are too slow for most process control applications.

SUMMARY OF THE INVENTION

One object of the present invention is to provide a method to predict the mechanical strength of dry wood from green or wet wood VIS-NIR spectra from a calibration model using multivariate analysis.

Another object of the present invention is to provide a method which is useful in a manufacturing process, for quality control and process monitoring of a green feedstock or product, based on the mechanical properties of dry wood predicted from VIS-NIR spectra.

A further object of the present invention is to provide a rapid, accurate method for predicting the mechanical properties of standing trees, which is useful in assessing the value of a stand of timber, by quantitatively measuring the quality of the timber via VIS-NIR spectra.

A still further object of the present invention is to provide a method, which is useful in making timber thinning and harvesting decisions via VIS-NIR spectra.

An additional object of the present invention is to provide an apparatus for determining the dry mechanical strength of green wood.

The present invention overcomes the problems of the prior art methods by providing a method for predicting the dry mechanical strength for a green wood, comprising: illuminating a surface of the wood to be predicted, the wood having a green moisture content; analyzing the wood surface using VIS-NIR spectrometric method from a reduced range of wavelengths in the range of from about 400 to about 1,150 nm, the method generating a first spectral data; and using a multivariate analysis to predict the dry mechanical strength by comparing the first spectral data with a calibration model, the calibration model comprising a second spectrometric method of spectral data of a reduced range of wavelengths in the VIS-NIR spectra obtained from a reference wood having a green moisture content, the second spectral data correlated with a known mechanical strength analytical result obtained from a reference wood when dried and having a dry moisture content.

The present invention also provides analysis of green wood utilizing a reduced range of wavelengths of VIS-NIR to enable use of lightweight portable instrument means extensively available on the market to facilitate "on the spot" analysis of VIS-NIR spectra for predicting dry mechanical strength from standing trees or wet wood.

In the context of the invention, the reduced range of wavelengths of VIS-NIR enables predicting mechanical and physical properties from standing trees or wet wood by taking VIS-NIR spectra from the radial face of a hole drilled into the wood from which VIS-NIR reflectance spectra are collected.

Also, in the context of the invention, both in-plant and in-field measurements that require very rapid spectral acquisition times between 10 microseconds and 1 second, or more, for effective process monitoring or field measurements is available through low-cost, lightweight spectrometers with very rapid acquisition times that are not available with spectrometers at VIS-NIR wavelengths above 1150 nm and associated with acquisition times of more than 3 seconds and therefore too slow for many process control applications.

BRIEF DESCRIPTION OF THE DRAWINGS

The accompanying drawings, which are incorporated in and constitute a part of the specification, illustrate preferred embodiments of the invention and, together with the description establish the principles of the improved inventive concept.

DESCRIPTION OF THE PREFERRED EMBODIMENTS

Figure 1:
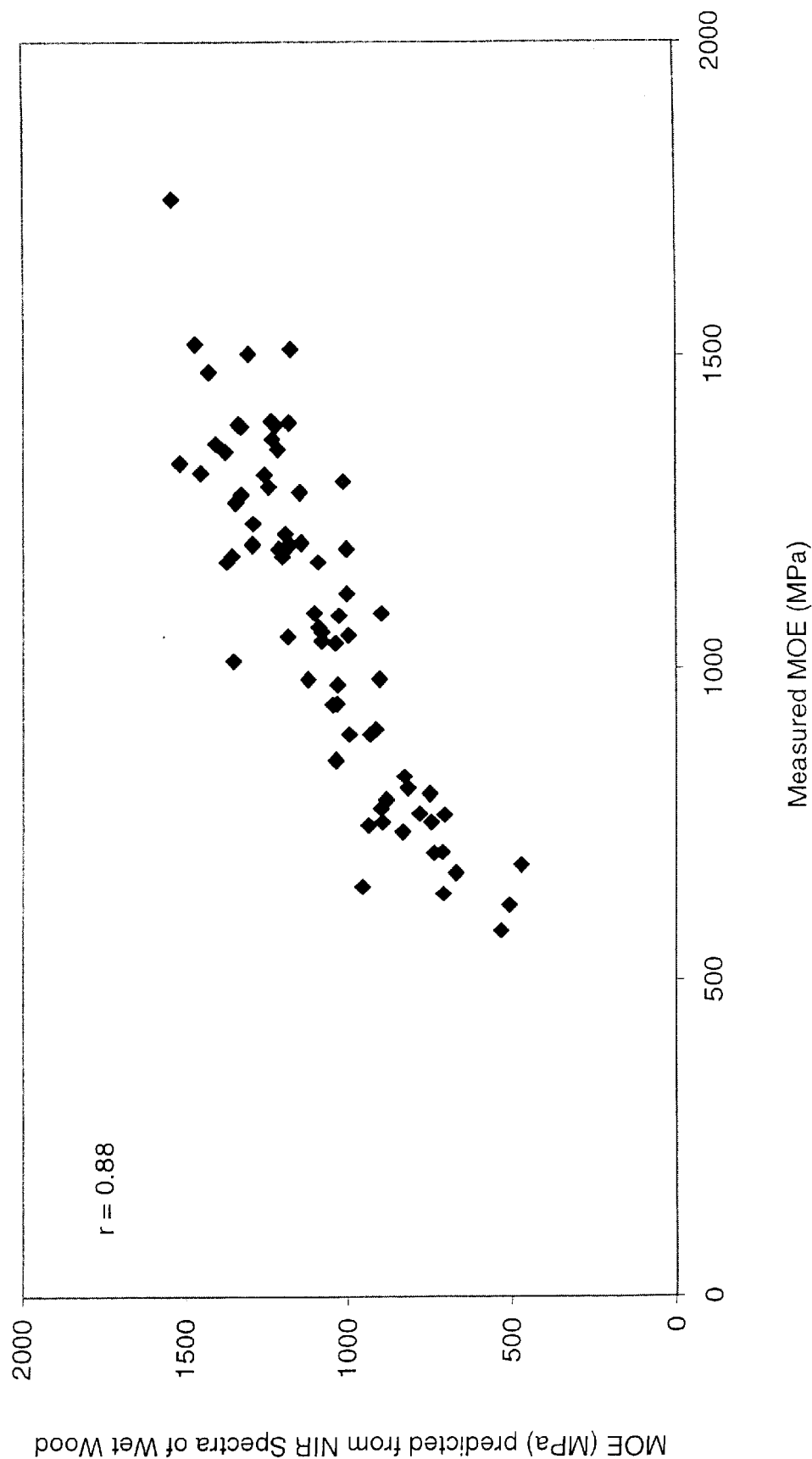
FIG. 1 is a plot of the measured MOE of dry mountain pines (Ponderosa and Lodgepole pine) regressed against the MOE predicted by a multivariate calibration model constructed with VIS-NIR spectra (400–2,500 nm) taken from wet Ponderosa and Lodgepole pines.

Unless specifically defined otherwise, all technical or scientific terms used herein have the same meaning as commonly understood by one of the ordinary skill in the art to which this invention pertains. Although any methods and materials similar or equivalent to those described herein can be used in the practice of the present invention, the preferred methods and materials are now described.

In general, the present invention provides a VIS-NIR method to predict the mechanical strength of dry processed wood products, e.g., veneers, flakes, or chips, from wet feedstock and to use this method to predict the strength or value of standing trees and logs, or to improve a process for manufacturing lumber or veneers. For example, the ability to sort wet wood products, based on their dry mechanical properties, would provide for a more efficient use of the resource. In this manner, veneers with high MOE values could be sorted for use as outer plys of a laminated veneer lumber, with veneers having a lower MOE sorted for use as the center ply. Moreover, prediction of the dry strength of a wood product from the VIS-NIR spectra of wet wood is accomplished over a wide range of moisture contents.

Further, the invention method predicts the strength of wood for standing trees, in situ. VIS-NIR spectra, of wet wood or living tree, collected through a fiber-optic probe, are used to predict the dry wood properties of a living tree. This method allows development of a commercial system for predicting the strength of standing trees, which should directly translate into increasing their value as a manufacturing feedstock. Thus, it is intended that presently available portable VIS-NIR systems that can be used in the field would allow a forester to quantitatively measure the volume and quality of a stand of trees. The measured quality, along with a measure of tree volume, will determine the value of the tree. This result is useful in making thinning, harvesting, and timber management decisions.

Woods are classified broadly as softwoods or hardwoods, where softwoods are also known as conifers or evergreens and hardwoods are also known as deciduous or broad-leaved trees. Softwood contains tube-like fibers orientated along the longitudinal axis (grain) and cemented together with lignin. Hardwoods contain more complex structures, such as storage cells, in addition to longitudinal fibers. Fibers in hardwoods are also much smaller and shorter than those in softwoods. Thus, the term "wood" as used herein means either soft or hard wood.

The mechanical properties of woods are influenced by moisture content and grain orientation. (Strengths of dry woods are approximately twice those of wet or green woods. Longitudinal strengths may be as much as 40 times higher than cross-grain strengths.) Moisture content (MC) is defined by the equation MC=(wet weight−oven dry weight)/oven dry weight. In general, wood is considered green if its moisture content is above 19%. Wood is generally considered to be dry when it has reached its equilibrium moisture content, generally between 12% and 15% moisture. Thus, it is understood herein that moisture is not totally absent when used in terms of the expression dry wood.

According to the invention, a sample of wood having unknown mechanical properties and a moisture content greater than 15% is analyzed by a spectrometric method resulting in spectral data, whereupon said spectral data are compared with a multivariate calibration model comprising reference spectral data from a reference wood material having a moisture content greater than 15% and known dry mechanical properties. The multivariate calibration model contains reference spectral data from the wet wood sample known analytical results for dry mechanical properties, such as MOE and MOR. The multivariate calibration models are constructed using techniques such as projection to latent structures (PLS) modeling to provide a method for rapidly and accurately predicting the dry mechanical strength of the unknown wet wood by means of multivariate analysis.

The present invention demonstrates the utility of using VIS-NIR techniques, coupled with multivariate calibration modeling techniques such as PLS, also known as partial least squares modeling, to predict the mechanical properties of wood. The mechanical strength of wood is a complex function of the chemical composition, density, moisture content, slope of grain, microfibril angle of the wood, and other wood features. The mechanical properties of interest desirably include, without limitation, MOE, MOR, toughness, compression strength, buckling strength, tensional strength and stiffness, shear strength, and screw or nail withdrawal load, generally measured, preferably, according to established ASTM standard protocols. Strength and elasticity may be expressed in the units $lbf/in^2$ (multiply $lbf/in^2$ by 6.894 to obtain kilopascal).

The VIS-NIR spectra provide quantitative information on these features, which can be extracted when the VIS-NIR spectra are subjected to PLS modeling, this technique gives a rapid and accurate method for measuring the mechanical strength of dry wood. The information provided by this technique is useful for forest harvesting and stand valuation, and in quality control and process monitoring.

This invention may be used as a rapid and accurate method for predicting the strength of standing trees and for predicting the mechanical properties of standing trees and for assessing the value of a stand of timber. Taken in conjunction with conventional measurements of the volume of a tree, this invention is useful to quantitatively measure the quality and value of the timber. Thus, the method herein may be used as an aid in making decisions, which relate to thinning and harvesting of woodlands. This method may also be used for characterizing the mechanical properties of standing trees or saw logs, and allocating them for their best use. This method may also be used in controlling a process for manufacturing a wood product or for sorting a feedstock or product.

Either use of the invention requires the production of a calibration model. This calibration model uses a set of "known" samples, which can then be used to predict the mechanical properties of unknown sample interest. The calibration model requires the VIS-NIR spectra of wet woods samples, drying these samples below 10% moisture content and measuring the mechanical properties of interest. These mechanical properties include but and are not limited to MOE and MOR. The objects of the calibration model used in the present invention may be obtained by first analyzing a wet veneer, solid wood sample, tree or log using a fiber-optic device, located normal to the sample surface, at a distance which provides an observation area in the range of about 0.2 in to 4 ft in diameter. The VIS-NIR reflectance at wavelengths in the range of 400–1,150 nm are obtained as an average of 20 –100 individual scans to produce a single VIS-NIR spectrum. The wet samples may range in moisture content between 15% and 100% and the VIS-NIR spectra are measured on the wet sample. The samples are then dried and may be formed into a shape that allows the mechanical properties to be measured. The mechanical properties of the dry solid wood, including MOE, MOR, toughness, compression strength buckling strength, tensional strength and stiffness, shear strength, screw or nail withdrawal load are then measured, preferably according to established ASTM standard protocols. The data derived from the wet spectra together with the dry mechanical strength analytical results are preferably input into a computer for use in a calibration model, which uses multivariate analysis to predict the mechanical strength of the dry sample from the wet spectra. Over the entire range of mechanical strengths and moisture contents, the VIS-NIR model is able to provide a very strong correlation between the actual and the predicted mechanical properties. The multivariate analysis of the invention herein may be performed according to Projection to Latent Structures (PLS), Principal Component Analysis (PCA), Partial Least Squares Regression (PLSR), Principal Component Regression (PCR), Multilinear Regression Analysis (MLR) or Discriminate Analysis, but preferably using Projection to Latent Structures. Various programs are available for performing the multivariate analysis herein, including the program of The Unscrambler which is the registered trademark of Camo, Inc., Corvallis, Oreg.

The determination of dry MOE and MOR from a spectrum of an unknown wet solid wood sample by use of the spectrometric measurement comprises two main steps. The calibration model described above provides for the development of calibration sets, data processing, and analysis by the use of actual measurements of the spectra from wet samples, bench testing of the actual MOR and MOE for the dry samples, and construction of the calibration model. The second main step is the spectrometric analysis of an unknown wet sample, such as a tree, log, solid wood or veneer, spectral data processing, optionally followed by data analysis, and application of the calibration model, developed in the first main step, to the spectral data obtained from the uknown wet sample. Detailed examples generally relating to the development of a calibration model using multivariate analysis are described in U.S. Pat. Nos. 5,965,888; 5,638,284; 5,680,320; and 5,680,321, the disclosures of which are incorporated herein by reference.

A data output set may, but need not be included in the method of the invention. When used, data output may be according to any means well known, such as a cathode-ray tube, recording instrument, or signal means such as a diode, lamp, or current. For example, an analog to digital or digital to analog converter responsive to a signal, such as a 5 millivolt or other appropriate input or output voltage, may be used in an electrical connection with the invention herein for a direct-digital-control application in a process of sorting a wood product according to its mechanical properties.

The method herein may also be applied in a method for controlling process variables, which influence the strength of a dry solid wood product derived from a raw wet wood feedstock. For example, the present method may be used to determine the mechanical properties, including MOE and MOR, of dry lumber, which information is then fed into a system for controlling the wet feedstock into the process. It is also contemplated in the context of the invention to design a control system in which the obtained spectra optionally, after having reduced noise or base line drift or other manipulation of the spectral data of the wet wood, to input directly into the system for setting the process variable without having translated the spectra into a dry strength data. This is suitably accomplished by establishing a calibration model in which process variables are expressed as functions of dry wood strength and the spectral data, and then using the model in the actual production, at which spectral data are obtained from the wet material, and linked with desired dry product structural strength to give a product of the necessary quality.

The spectrometric measurements can be performed by an on-line, in-line or at-line optical fiber device, or by taking individual samples for separate analysis. In any case, the spectra are subject to further data treatment to reduce noise or improve the quality of the spectra. It is to be understood that the radiation used in the spectrometric method impinges directly on raw material on the solid wood based sample.

By way of illustration, a device is placed at a distance from the wet sample, containing a light source, detector, electronic components, and other well known components used to transmit a signal through or reflected on or partly through the sample. The resulting signals are returned to the detector in an accompanying optical fiber cable, and recorded.

In a spectrometer, the light is converted into an electric signal which consists of intensity verses wavelength that is then conveyed to a computer, where the spectrum of a previously stored reference sample can be related to the sample spectrum and a reference corrected spectrum is calculated. Correction of the spectrum may be performed by chemometrical methods, well known in the art, such as the description set forth in U.S. Pat. No. 5,638,284, the disclosure of which is incorporated herein by reference. In this invention, preferably, a spectrometer having a usable wavelength is the range of 400–1,150 nm is used. However, a scanning instrument, a diode array instrument, a Fourier transform instrument or any other similar equipment known in the art, may be used in accordance with the present invention.

An evaluation of wavelengths, which contains absorption, reflectance or transmission data, provides the relevant features for the analysis. By the application of chemometrical methods to the obtained spectra it is possible to ignore wavelengths which do not contain information that contribute to the chemical analysis, even though the measurement will include information from the entire wavelength range.

When used for timber management or harvesting decision the system may consist of a hand-held device with a fiber optic cable capable of carrying light into the unknown wet wood sample and also carrying the VIS-NIR signal back from the sample. The calibration model for this device is constructed as described above. This device can be hand-held and output to a lamp that is an instantaneous indicator of an analytical result which is useful in assisting the operator in making a timber purchase, thinning, or harvesting decisions.

EXAMPLE

The following examples illustrate the manner in which the method in accordance with the present invention can be made and used. Subsamples were obtained from short logs, taken from three live pine trees. Trees 1 and 3 were identified as Ponderosa Pine, and tree 2 was identified as a Lodgepole Pine. Two short logs were taken from each tree. One log was taken just above the base of the tree, at about 6-ft, and the second log was taken at about 20 ft, the location for these logs varied slightly to minimize defects within the log. Subsamples measuring between 10 and 24 inches long, 2 inches wide and one-quarter inch thick were produced and the VIS-NIR spectra were obtained on the wet samples. The subsamples were then dried and the ultimate mechanical properties, e.g., MOE and MOR, were measured on the dry samples. The absorption spectra of the wet samples and the mechanical properties of the dry samples were used to construct a multivariate calibration model that could be used to predict the dry mechanical properties of unknown samples from their wet VIS-NIR spectra. The mechanical properties of both species were predicted from a single model.

FIG. 1 shows a plot of the measured MOE of dry Ponderosa and Lodgepole pines regressed against the MOE predicted by a multivariate calibration model constructed with VIS-NIR spectra taken from wet Ponderosa and Lodgepole pines.

Figure 2:
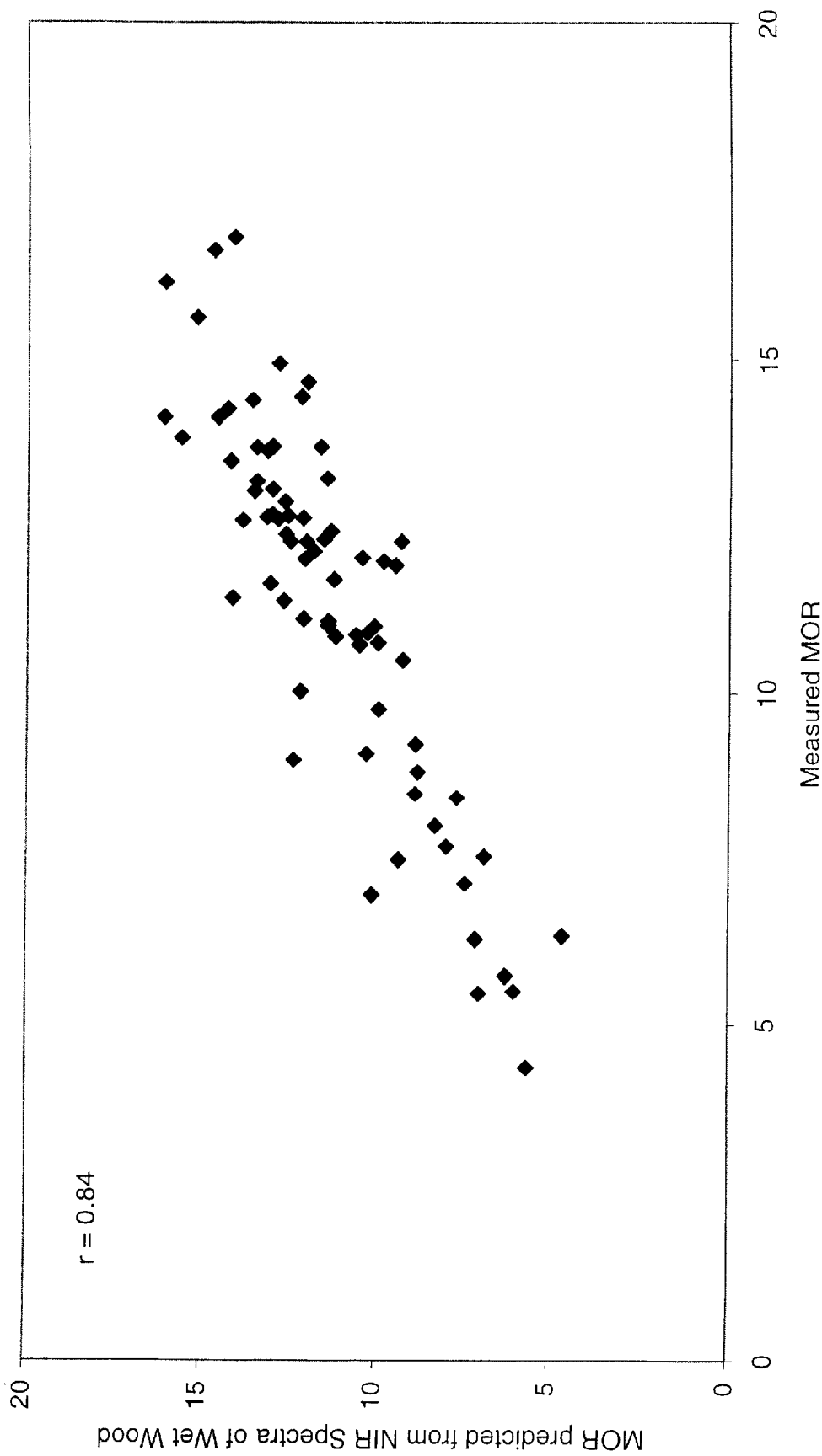
FIG. 2 is a plot of the measured MOR of dry mountain pines (Ponderosa and Lodgepole pine) regressed against the MOR predicted by a multivariate calibration model constructed with VIS-NIR spectra (400–2,500 nm) taken from wet Ponderosa and Lodgepole pines.

FIG. 2 shows a plot of the measured MOR of dry Ponderosa and Lodgepole pines regressed against the MOR predicted by a multivariate calibration model constructed with VIS-NIR spectra taken from wet Ponderosa and Lodgepole pines.

Finally, a set of five Slash pine trees were harvested. Short logs were cut from four or five locations along the height of the trees, approximately every 16 ft. VIS-NIR spectra of the wet wood were obtained from radial face of the wet wood with a fiber optic device connected to the VIS-NIR spectrometer. More than 300 samples were then cut from the wet logs and the VIS-NIR spectra of the wet wood were measured with a fiber optic VIS-NIR system. The samples were then dried and their dry mechanical properties were measured, e.g., MOR and MOE. The spectra of the wet samples and the mechanical properties of the dry samples were used to construct a multivariate calibration model that could be used to predict the dry mechanical properties of unknown samples from their wet VIS-NIR spectra. VIS-NIR spectra from either the probe equipped with the prism to project the VIS-NIR beam at 90° and the VIS-NIR spectra taken directly from the wet surface of the freshly cut sample can be used to construct a multivariate calibration model that may be used to predict the dry mechanical properties of unknown samples from their wet VIS-NIR spectra.

As can be seen, two sets of samples were analyzed. The first set of samples came from three pine trees cut from a stand in Evergreen, Colo. and are referred to as the "Mountain Pine" sample set.

The second set of samples came from five Slash pine trees cut in Arkansas and is referred to as the "Slash Pine" sample set.

Figure 3:
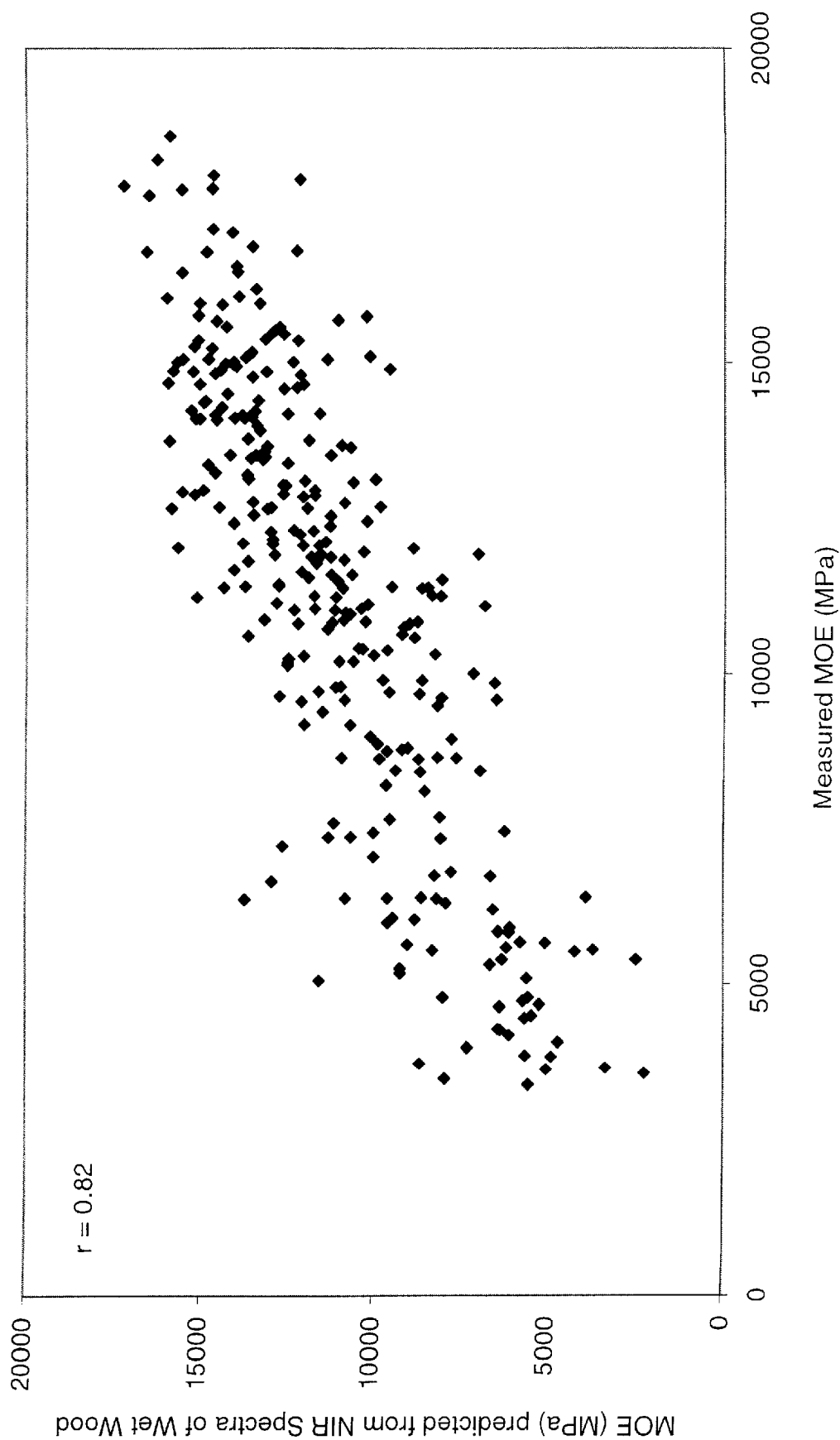
FIG. 3 is a plot of measured MOE of dry Slash pine regressed against the MOE predicted by a multivariate calibration model constructed with VIS-NIR spectra (400–2,500 nm) taken from wet Slash pine.

Referring now to FIG. 3, a plot of the measured MOE of dry Slash Pine is shown as regressed against the MOE predicted by a multivariate calibration model constructed with VIS-NIR spectra taken from wet Slash Pine.

Figure 4:
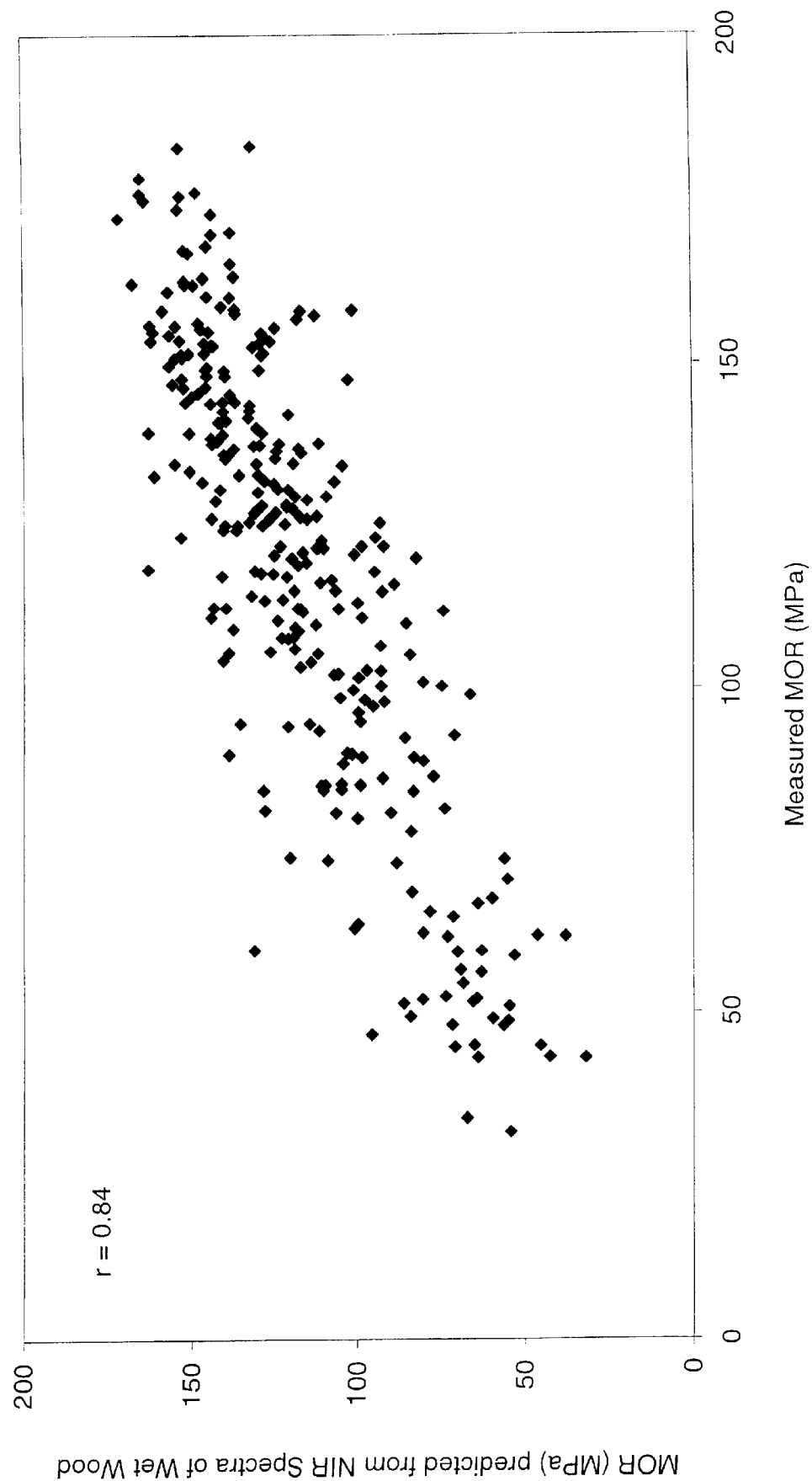
FIG. 4 is a plot of the measured MOR of dry Slash pine regressed against the MOR predicted by a multivariate calibration model constructed with VIS-NIR spectra (400–2,500 nm) taken from wet Slash pine.

In FIG. 4, a plot of the measured MOR of dry Slash Pine is shown regressed against the MOR predicted by a multivariate calibration model constructed with VIS-NIR spectra taken from wet Slash Pine.

The improvements beyond the prediction results in FIG. 4 relies upon the important developments of: the ability to predict the mechanical properties of green wood or standing trees from a reduced range of wavelengths; the ability to predict the properties of standing trees from a probe inserted into the tree of from spectra taken from a "bark window"; and the capability of using a low-cost, VIS-NIR spectrometer that can be used to collect spectra rapidly with smaller portable units.

More specifically, the improvement utilizes wavelengths between about 400 to about 1,150 nm (more preferably 400 to 1,000 nm), and there are commercially available low cost, light-weight spectrometers with very rapid acquisition times operating in this spectral range.

While wavelengths between 400 and 1,150 nm are preferred and contain overtones of many different carbon-hydrogen and hydroxyl vibrations, the exact assignment of specific chemical groups is not required for effective use of this wavelength range in the practice of the invention. Nevertheless, the improvement utilizes data processing algorithms such as PLS or PLSR modeling to predict the mechanical properties of wood and does not require precise assignment of the individual vibrations to specific chemical groups.

Instead, in this improvement, the wavelength range was also selected based upon the spectral range obtained with less expensive, lightweight, durable diode array detectors. The good correlations that were observed are substantially in the visible region of the spectra (400–700 nm) that is commonly thought to contain only information about the color of a sample. This spectral range and the short VIS-NIR region (400–1,150 nm) also contains chemical information on the hydroxyl groups, carbon-hydrogen bonds on the carbohydrates, and lignin present in the wood in the form of third and fourth overtone vibrations. It is this subtle chemical information that the models exploit for predicting the mechanical properties of the wood.

The second part of the improvement depends on acquiring VIS-NIR spectra with a fiber optic probe inserted into the tree or VIS-NIR spectra taken from the outer most layer of wood and used to predict the strength and stiffness of the tree. The significance of this second part of the improvement is that it enables field sampling of trees in a realistic manner. When the fiber optic probe is inserted into the tree, the spectra are collected using a fiber optic device that has a prism attached to it's end. This probe allows spectra to be collected from an interior region of the tree, preferably, from the radial face of the wood. The prediction derived from spectra taken in this manner makes rapid field acquisition of spectra practical.

The third part of the improvement involves the use of low-cost lightweight, spectrometers with very rapid acquisition times. The improved spectrometers contain no moving parts and are very durable and reliable, whether in the field or in a plant environment. These spectrometers are readily available commercially but use of these spectrometers in the context of the invention for both in-plant and in-field measurements of wet wood is novel. In-plant measurements of solid wood require very rapid spectral acquisition times that are typically between 10 microseconds and 1 second, or more, for effective process monitoring. This is so because in-plant processing typically involves rapidly moving pieces, and if the spectral acquisition times are too long the portion of the piece under the spectral view will change greatly, thereby decreasing the quality of the spectra and the quality of the resulting prediction.

On the other hand, while the original spectra of the base invention were collected with a portable spectrometer (Analytical Spectral Devices Field Spec), it is still relatively heavy for practical field work. The acquisition time for the original spectra (350–2,500 nm) from the portable instrument (Analytical Spectral Devices Field Spec) was typically 1–3 seconds, and therefore too slow for many process control applications.

Finally, the improved invention also includes the use of advanced data processing algorithms, such as orthogonal signal correction and wavelet transformation, which can improve the quality of the predictive models. This advanced data analysis technique reduces the speed and memory size of the computer required for data processing in the actual spectrometer. Reducing the computational demands on the computer enables the use of smaller, less expensive computers, such as those contained in commercially available personal digital assistants for handheld VIS-NIR spectrometer measurements.

Figure 5:
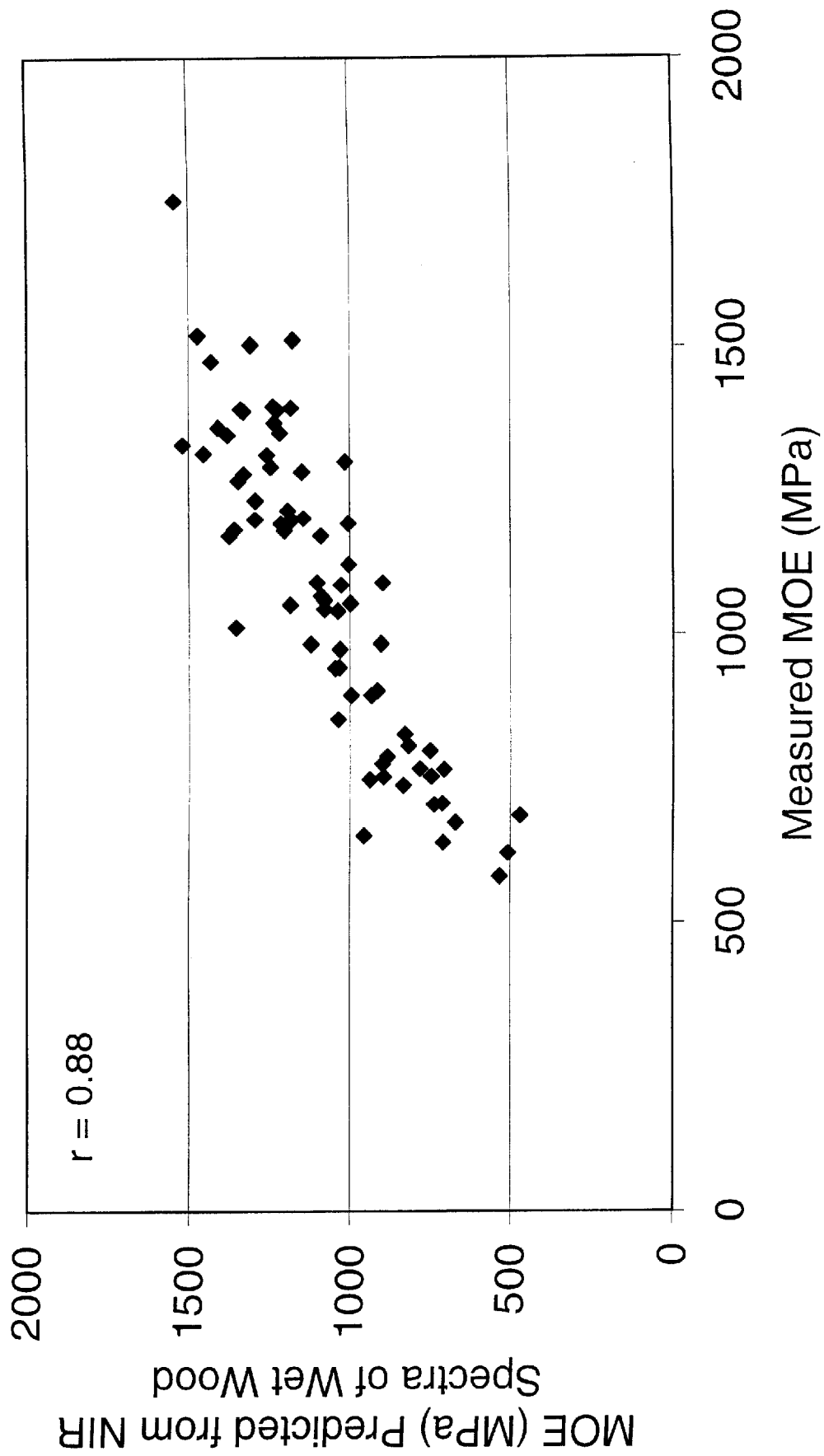
FIG. 5 is a graph of dry stiffness (MOE) of 74 Mountain pine samples predicted from the VIS-NIR spectra of wet wood. This prediction is based on a 2,150 nm range (350–2,500 nm) and is the base technology.

The dry stiffness (MOE) of 74 mountain pine samples are predicted from the VIS-NIR spectra of wet wood in FIG. 5. This prediction is based on 2,150 individual wavelengths and is the base technology.

Figure 6:
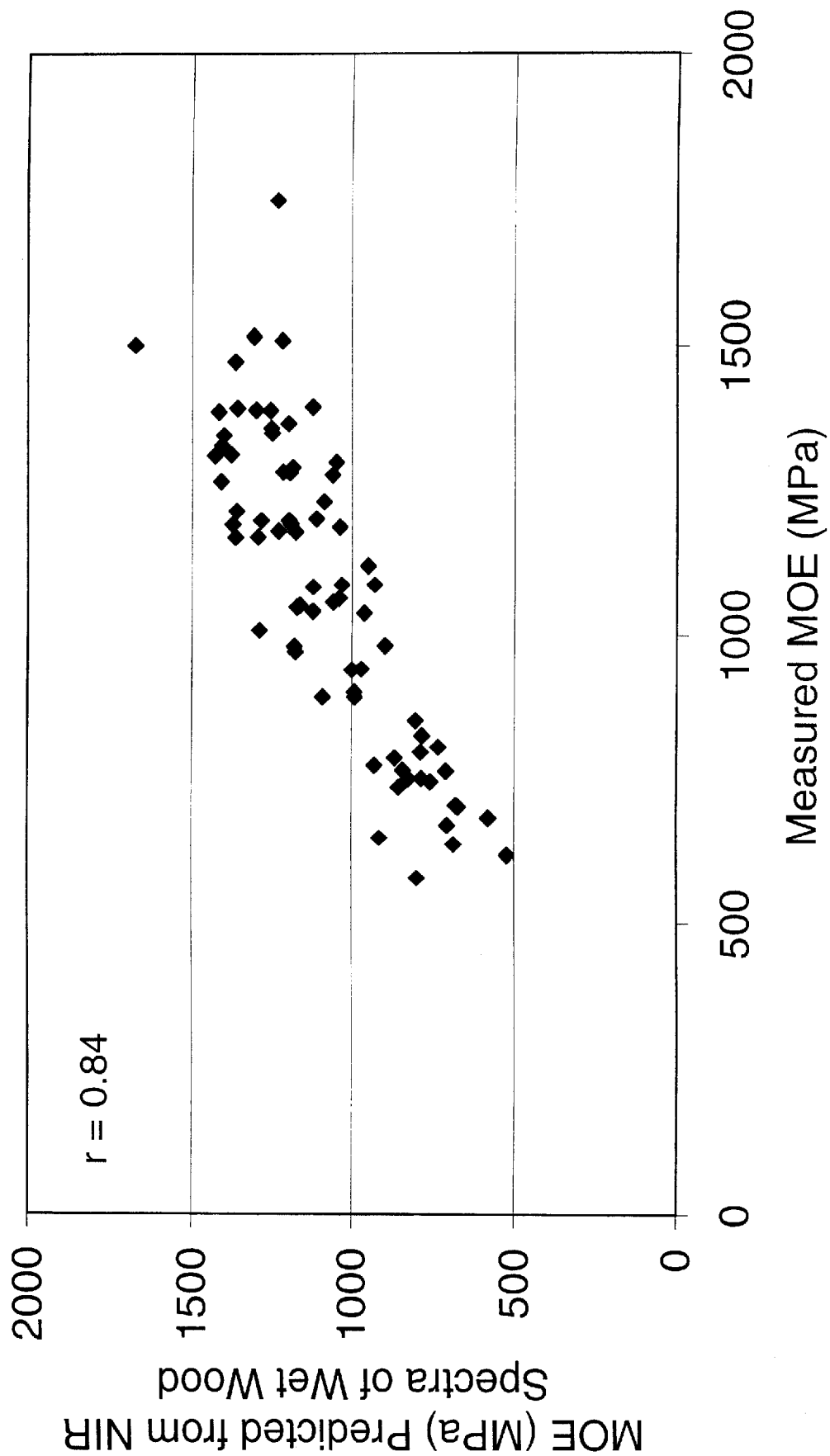
FIG. 6 is a graph of dry stiffness (MOE) of 74 mountain pine samples predicted from the VIS-NIR spectra of wet wood using a 750 nm range (400–1,150 nm) measured with a diode array detector.

FIG. 6 is a graph of the dry stiffness (MOE) of 74 mountain pine samples predicted from VIS-NIR spectra of wet wood. The prediction is based on only a 750 nm range (400–1,150 nm) that can be measured using the solid-state diode array detector only. This plot is an improvement over the basic technology since it only uses third and fourth overtones of the actual vibrations of interest and thereby enables use of very fast, inexpensive and light weight detectors.

Figure 7:
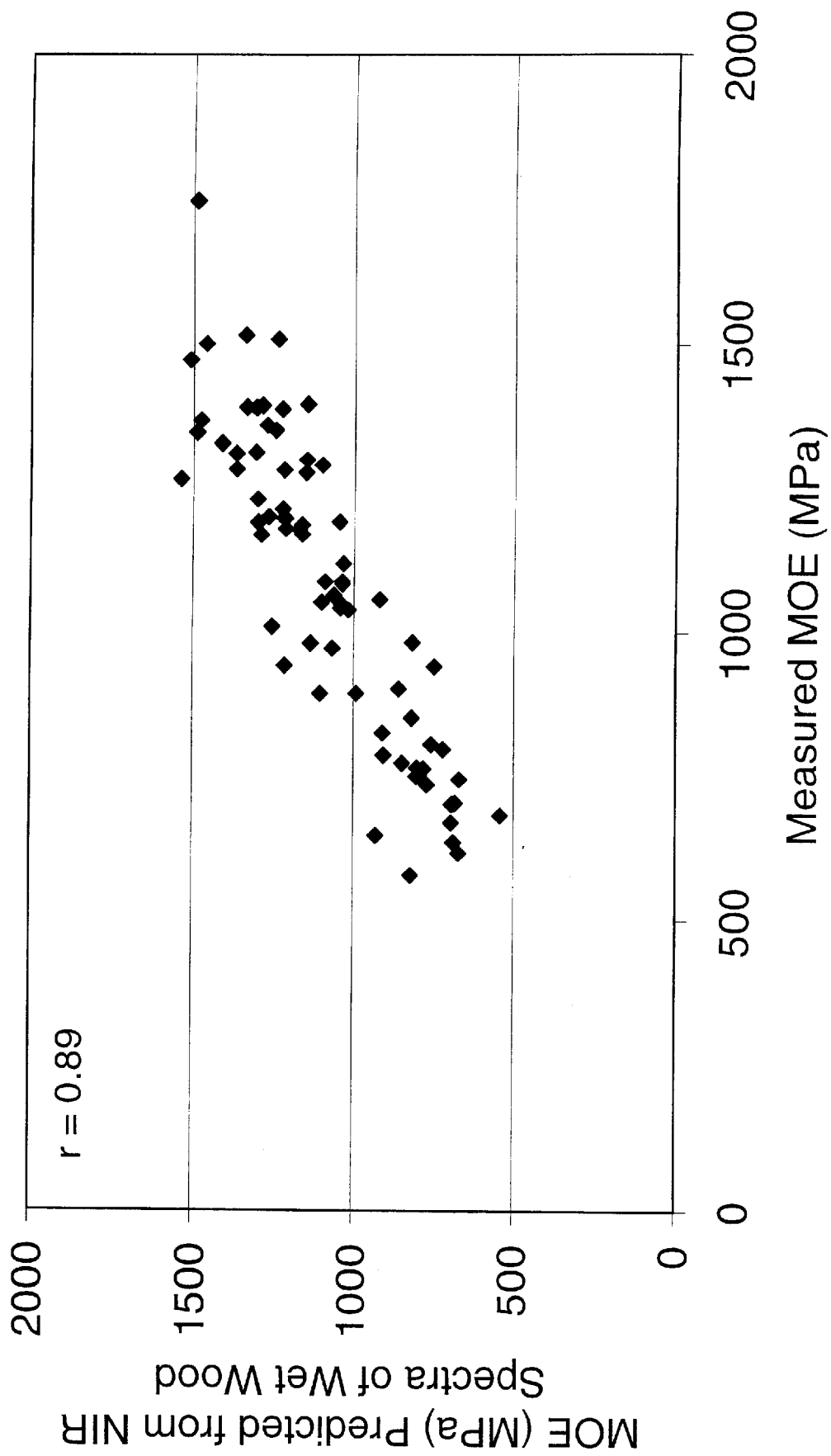
FIG. 7 is a graph of dry stiffness (MOE) of 74 mountain pine samples predicted from the VIS-NIR spectra of wet wood using a 450 nm range (500–950 nm) measured with diode a array detector.

A graph of the dry stiffness (MOE) of 74 mountain pine samples predicted from the VIS-NIR spectra of wet wood in FIG. 7. This prediction is based on a 450 nm range (500–950 nm) measured with a diode array detector only. This graph demonstrates improvement of the basic technology since it only uses third and fourth overtones of the actual vibrations of interest and thereby enables use of very fast, inexpensive and light weight detectors. The use of wavelengths between 500 and 950 nm provides better correlation than 400–1,150 nm since the noise contribution from light scatter in the ultraviolet range and short wavelength visible region has been eliminated.

Figure 8:
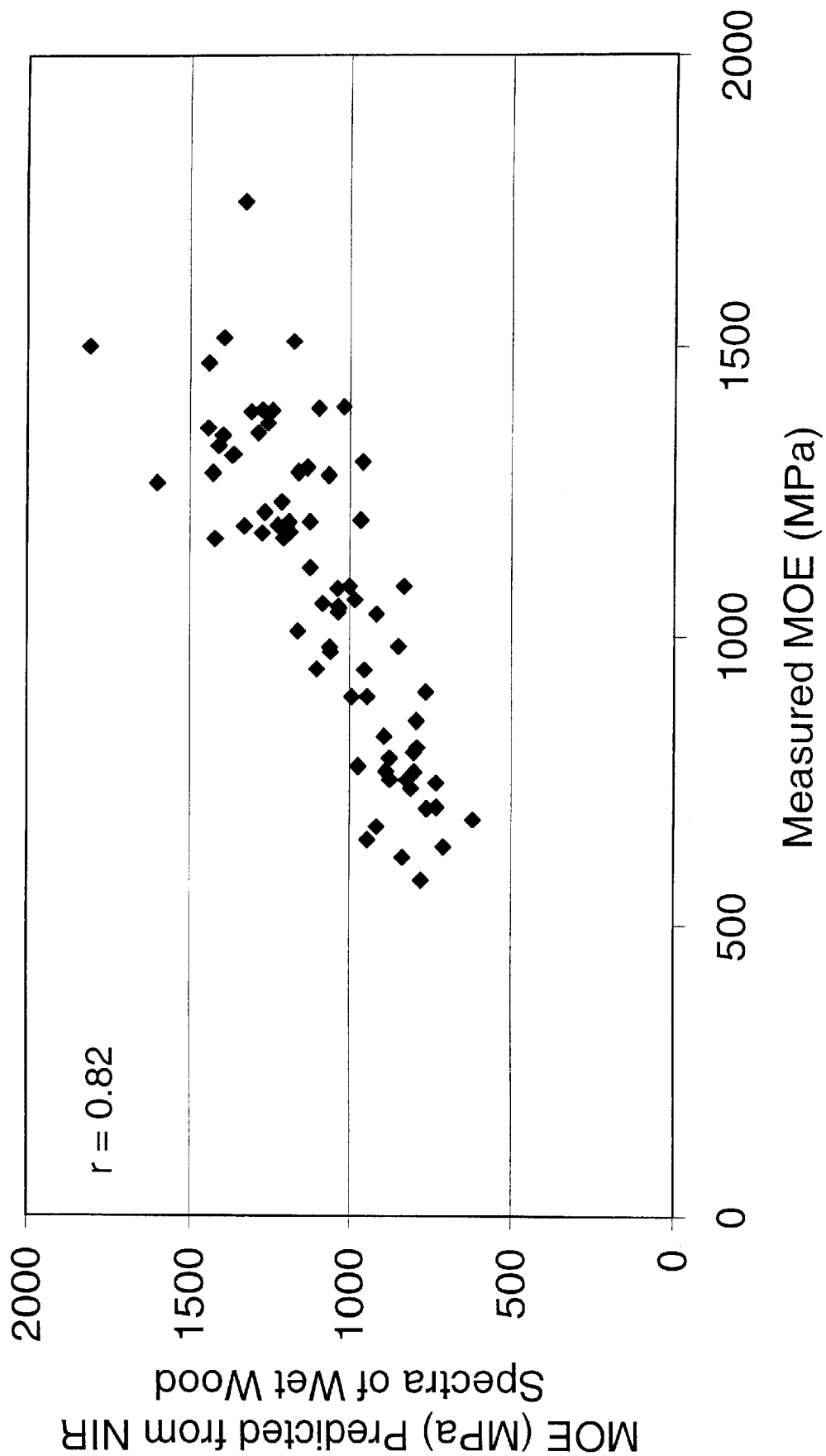
FIG. 8 is a graph of dry stiffness (MOE) of 74 mountain pine samples predicted from the visible spectra of wet wood using a 300 nm range (400–700 nm) measured with a diode a array detector.

FIG. 8 is a graph of the dry stiffness (MOE) of 74 mountain pine samples predicted from the VIS-NIR spectra of wet wood. This prediction is based on a 300 nm range (400–700 nm) and is measured with a diode array detector. This plot highlights the use of a very narrow spectral range, and shows that the scatter between 400–500 nm slightly reduces the strength of the prediction.

Figure 9:
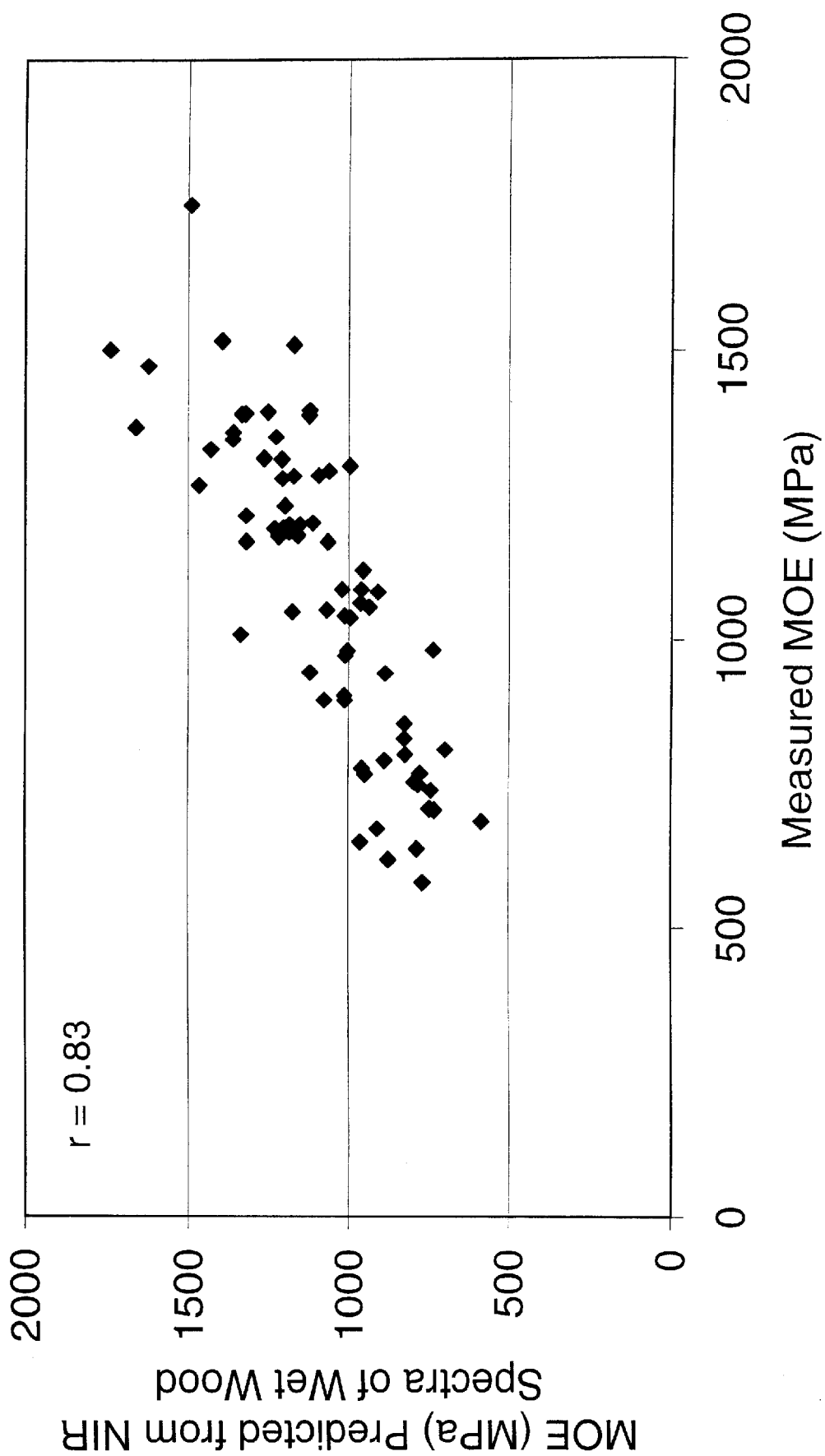
FIG. 9 is a graph of dry stiffness (MOE) of 74 mountain pine samples predicted from the VIS-NIR spectra of wet wood using a 300 nm range (500–800 nm) measured with diode a array detector.

A graph of the dry stiffness (MOE) of 74 mountain pine samples is predicted from the VIS-NIR spectra of wet wood as shown in FIG. 9. This prediction is based on a 300 nm range (500–800 nm) and is measured with a diode array detector (solid-state diode array detector only). This plot highlights the use of a very narrow spectral range.

Figure 10:
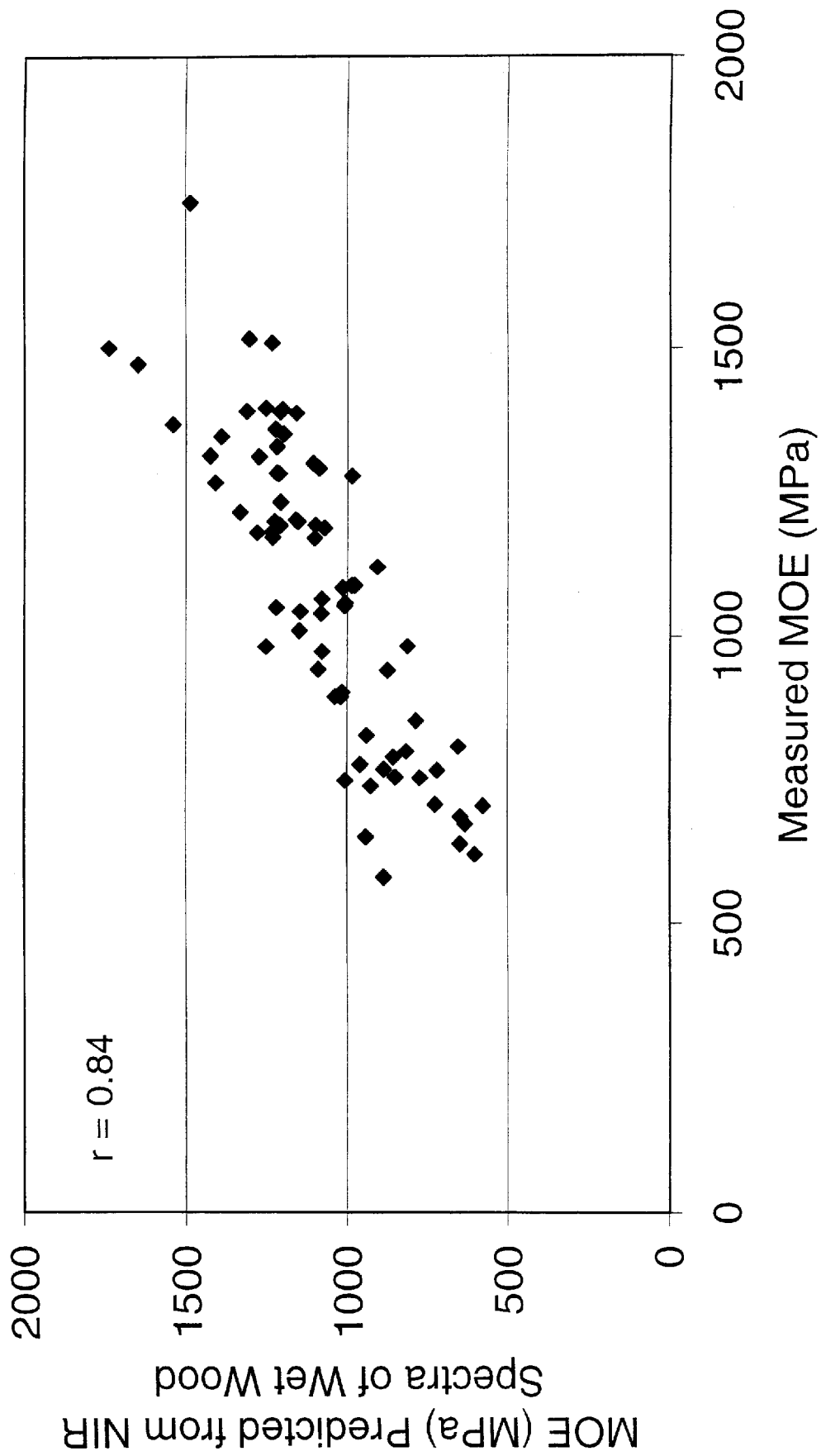
FIG. 10 is a graph of dry stiffness (MOE) of 74 mountain pine samples predicted from the VIS-NIR spectra of wet wood using a 300 nm range (600–900 nm) measured with a diode array detector.

FIG. 10 is a graph showing the dry stiffness (MOE) of 74 mountain pine samples predicted from VIS-NIR spectra of wet wood. The prediction is based on a 300 nm range (600–900 nm) and is measured with a solid-state diode array detector only. The plot highlights the use of a very narrow spectral range.

Figure 11:
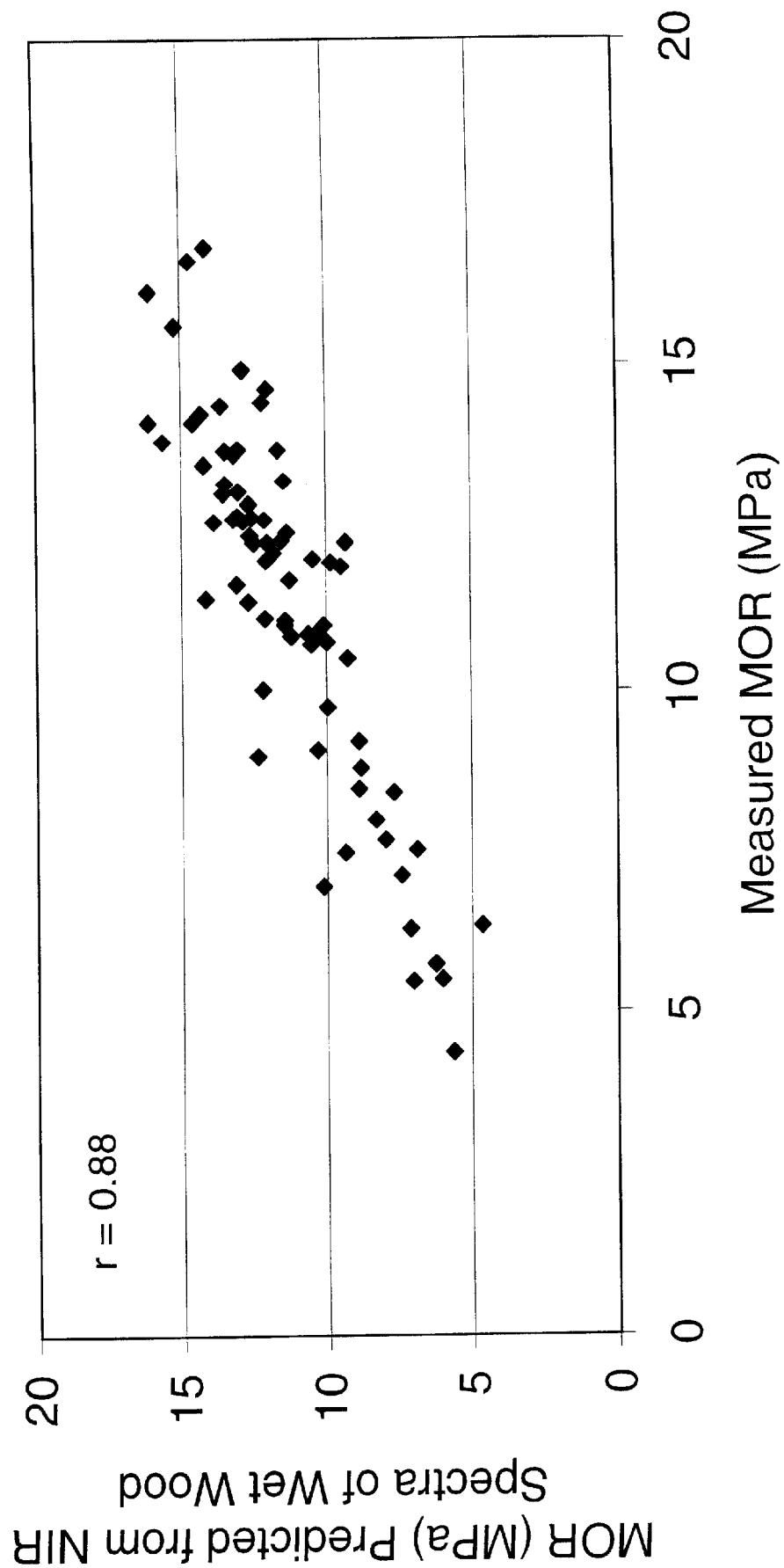
FIG. 11 is a graph of ultimate strength MOR of 74 mountain pine samples predicted from the VIS-NIR spectra of wet wood using a 2,150 nm range (350–2,500 nm) and is the base technology.

A graph of the measured ultimate strength (MOR) of 74 mountain pine samples is predicted from VIS-NIR spectra of wet wood in FIG. 11. This prediction is based on a 2,150 nm range and represents the basic technology.

Figure 12:
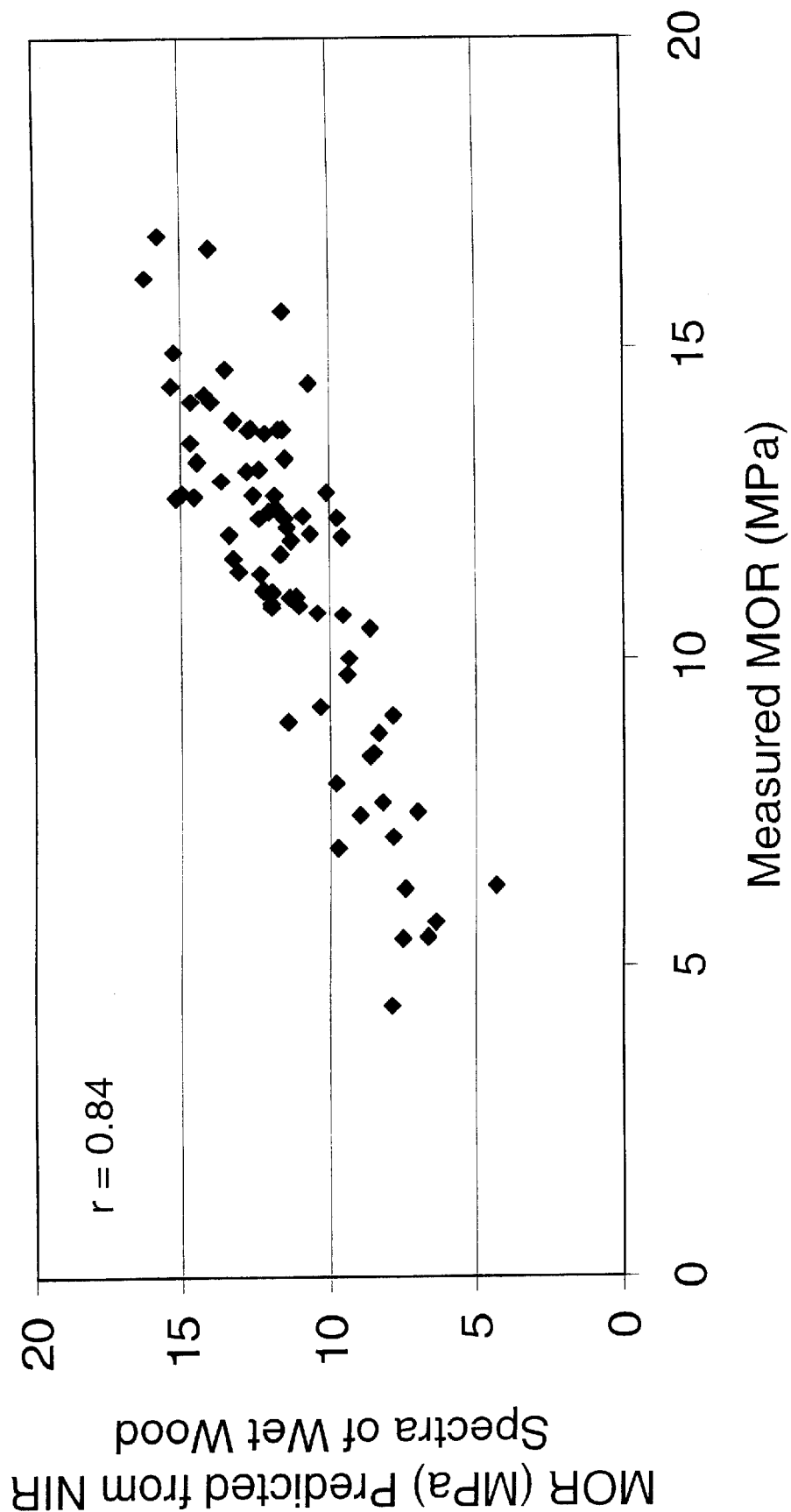
FIG. 12 is a graph of ultimate strength (MOR) of 74 mountain pine samples predicted from the VIS-NIR spectra of wet wood using a 750 nm range (400–1,150 nm) measured with a diode array detector.

FIG. 12 is a graph of the measured ultimate strength (MOR) of 74 mountain pine samples predicted from the VIS-NIR spectra of wet wood. This prediction is based on a 750 nm range (400–1,150 nm) that can be measured with a solid-state diode array detector. This plot is an improvement in the technology since it uses only third and fourth overtones of the actual vibrations of interest and thereby enables use of very fast, inexpensive and lightweight detectors.

Figure 13:
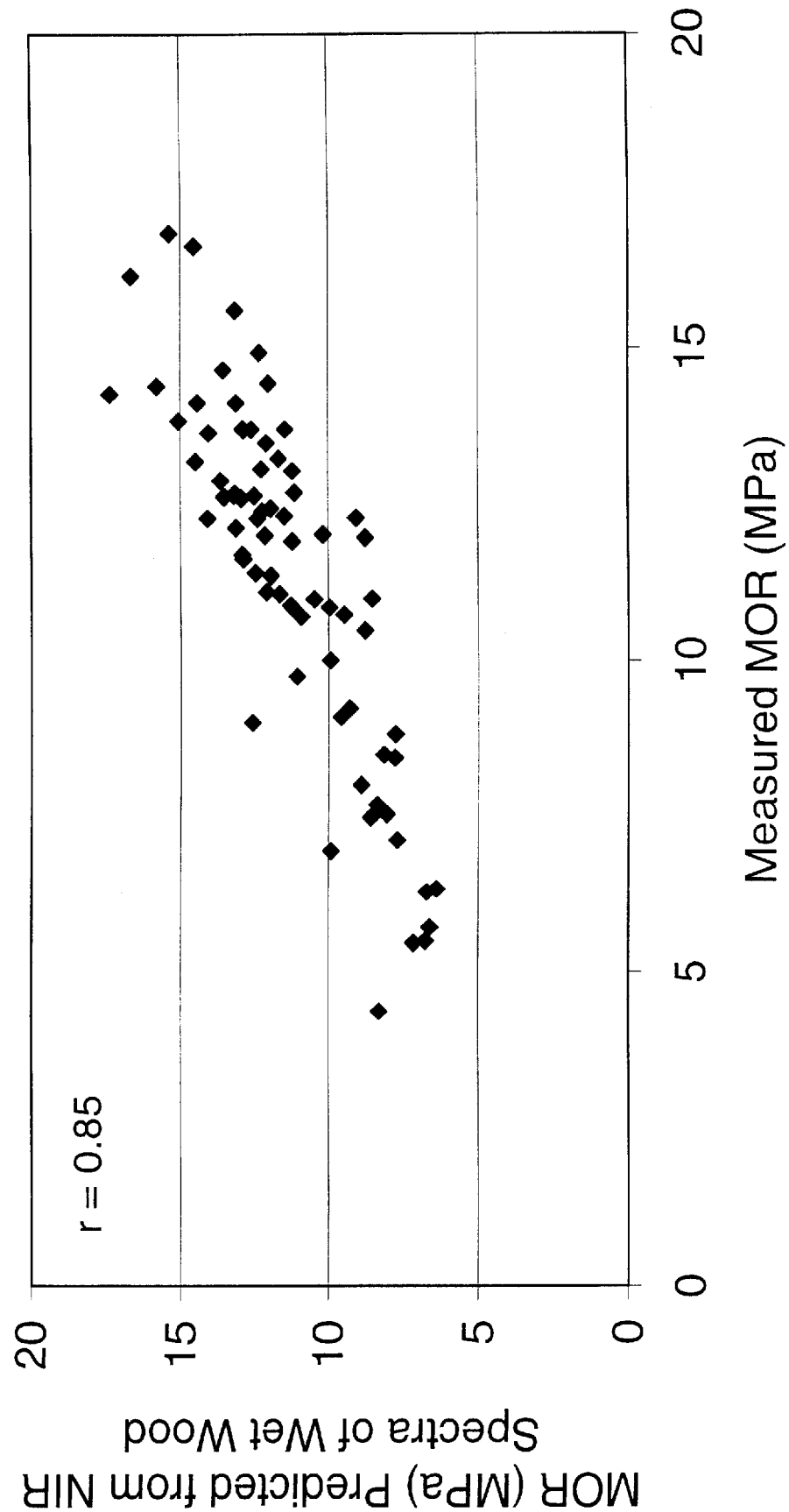
FIG. 13 is a graph of ultimate strength (MOR) of 74 mountain pine samples predicted from the VIS-NIR spectra of wet wood using a 450 nm range (500–950 nm) measured with a diode array detector.

A graph of the measured ultimate strength (MOR) of 74 mountain pine samples predicted from VIS-NIR spectra of wet wood is shown in FIG. 13. This prediction is based on a 450 nm range (500–950 nm) and measured with a solid-state diode array detector. This plot demonstrates the improvement in the basic technology since it uses only third and fourth overtones of the actual vibrations of interest and thereby enables use of very fast, inexpensive and lightweight detectors. Use of wavelengths between 500 and 950 nm gives a better correlation than 400–1,150 nm since light scatter in the ultraviolet range and short visible region is eliminated.

Figure 14:
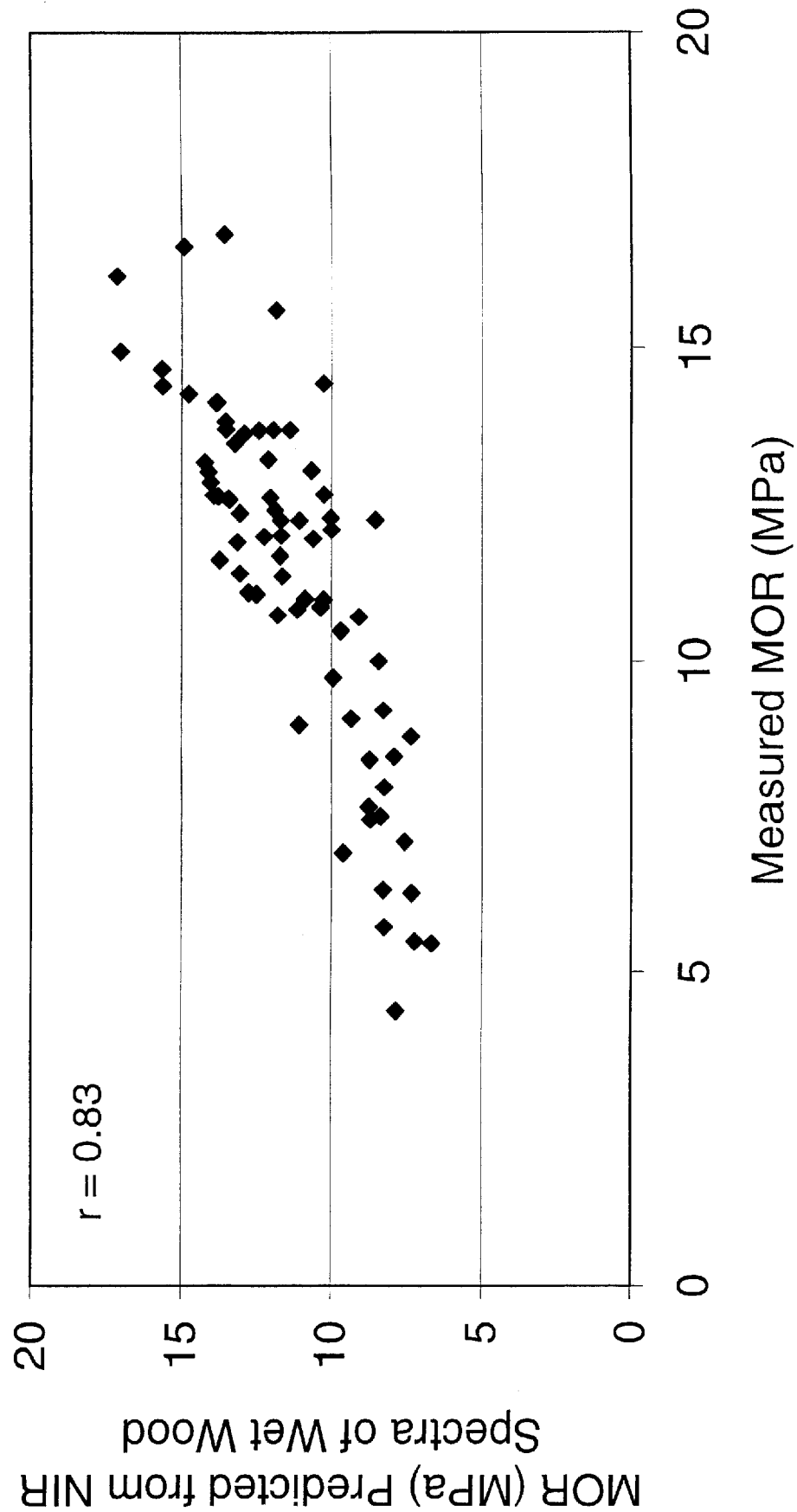
FIG. 14 is a graph of ultimate strength (MOR) of 74 mountain pine samples predicted from the VIS-NIR spectra of wet wood using a 300 nm range (400–700 nm) measured with a diode array detector.

A graph of the measured ultimate strength (MOR) of 74 mountain pine samples is predicted from the VIS-NIR spectra of wet wood are shown in FIG. 14. This prediction is based on a 300 nm range (400–700 nm) and is measured with a solid-state diode array detector. This plot highlights the use of a very narrow spectral range, and shows that scatter between 400–500 nm slightly reduces the strength of the correlation.

Figure 15:
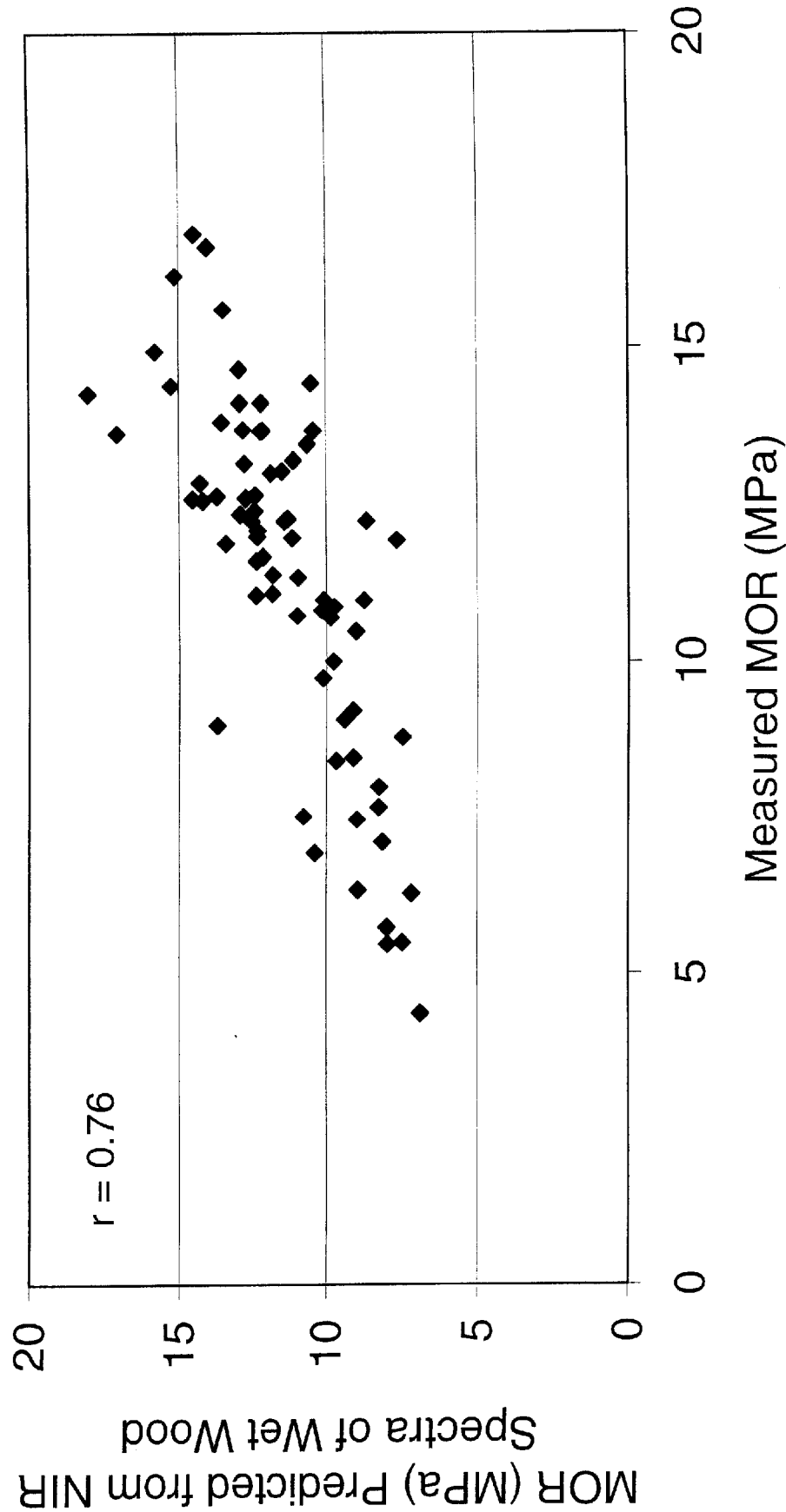
FIG. 15 is a graph of ultimate strength (MOR) of 74 mountain pine samples predicted from the visible spectra of wet wood using a 300 nm range (500–800 nm) measured with a diode array detector.

FIG. 15 is a graph of the measured ultimate strength (MOR) of 74 mountain pine samples predicted from VIS-NIR spectra of wet wood. This prediction is based on 300 nm range (500–800 nm) and is measured with a solid-state diode array detector. This plot highlights the use of a very narrow spectral range.

Figure 16:
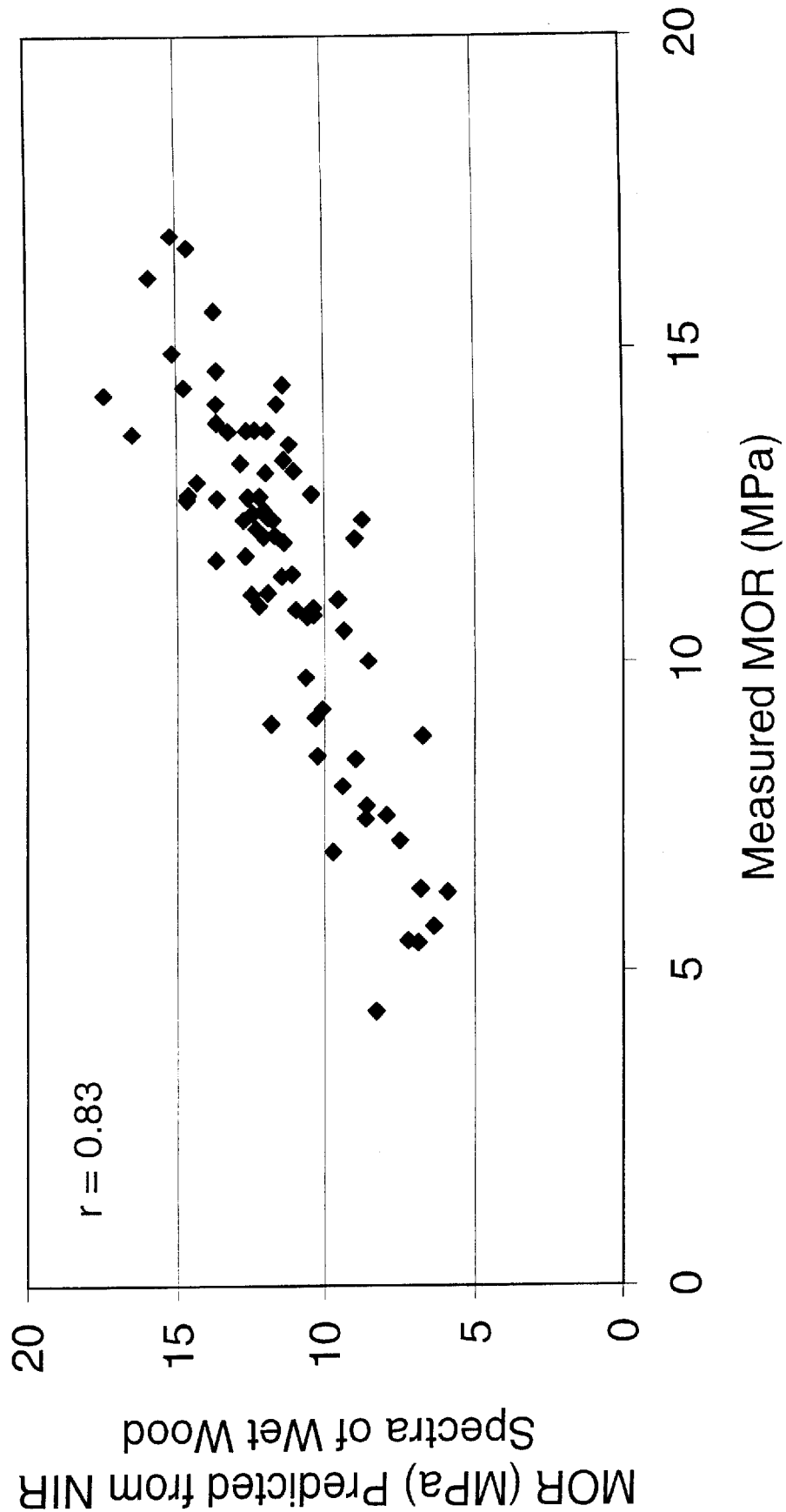
FIG. 16 is a graph of ultimate strength (MOR) of 74 mountain pine samples predicted from the VIS-NIR spectra of wet wood using a 300 nm range (600–900 nm) measured with a diode array detector.

A graph of the measured ultimate strength (MOR) of 74 mountain pine samples predicted from the VIS-NIR spectra of wet wood is shown in FIG. 16. This prediction is based on a 300 nm range (600–900 nm) and is measured with a solid-state diode array detector. This plot highlights the use of a very narrow spectral range.

Figure 17:
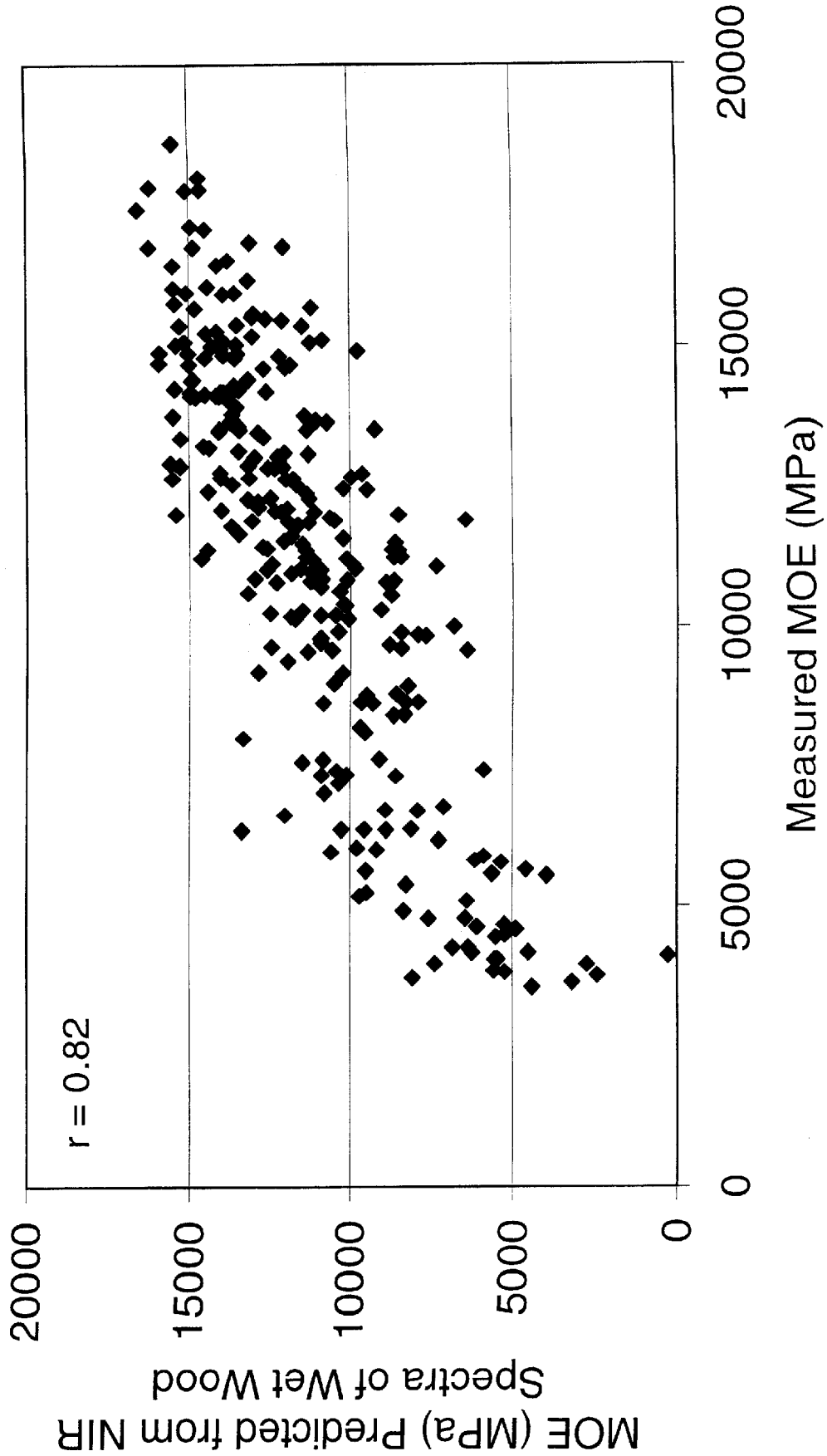
FIG. 17 is a graph of dry stiffness (MOE) of 278 Slash pine samples predicted from the VIS-NIR spectra of wet wood using a 2,150 nm range (350–2,500 nm) and is the base technology.

FIG. 17 is a graph of the dry stiffness (MOE) of 278 Slash Pine samples predicted from VIS-NIR spectra of wet wood. This prediction is based on a 2,150 nm range and represents the basic technology.

Figure 18:
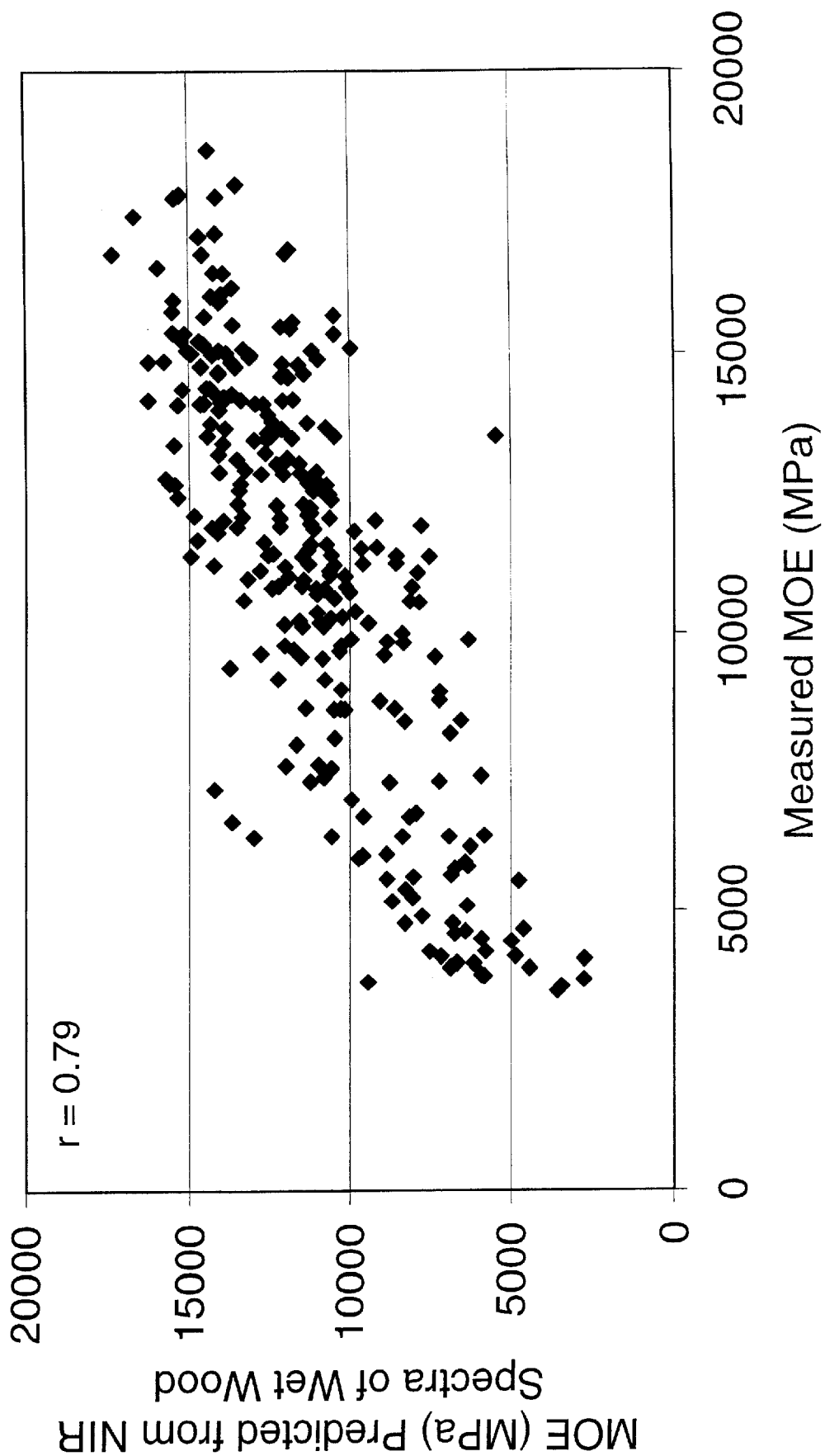
FIG. 18 is a graph of dry stiffness (MOE) of 278 Slash pine samples predicted from the VIS-NIR spectra of wet wood using a 750 nm range (400–1,150 nm) measured with a diode array detector.

A graph of the dry stiffness (MOE) of 278 Slash Pine samples is predicted from VIS-NIR spectra of wet wood is shown in FIG. 18. This prediction is based on a 750 nm range (400–1,150 nm) and can be measured with a solid-state diode array detector. This plot shows a dramatic improvement in the technology since it only uses third and fourth overtones of the actual vibrations of interest and thereby enables use of very fast, inexpensive and lightweight detectors.

Figure 19:
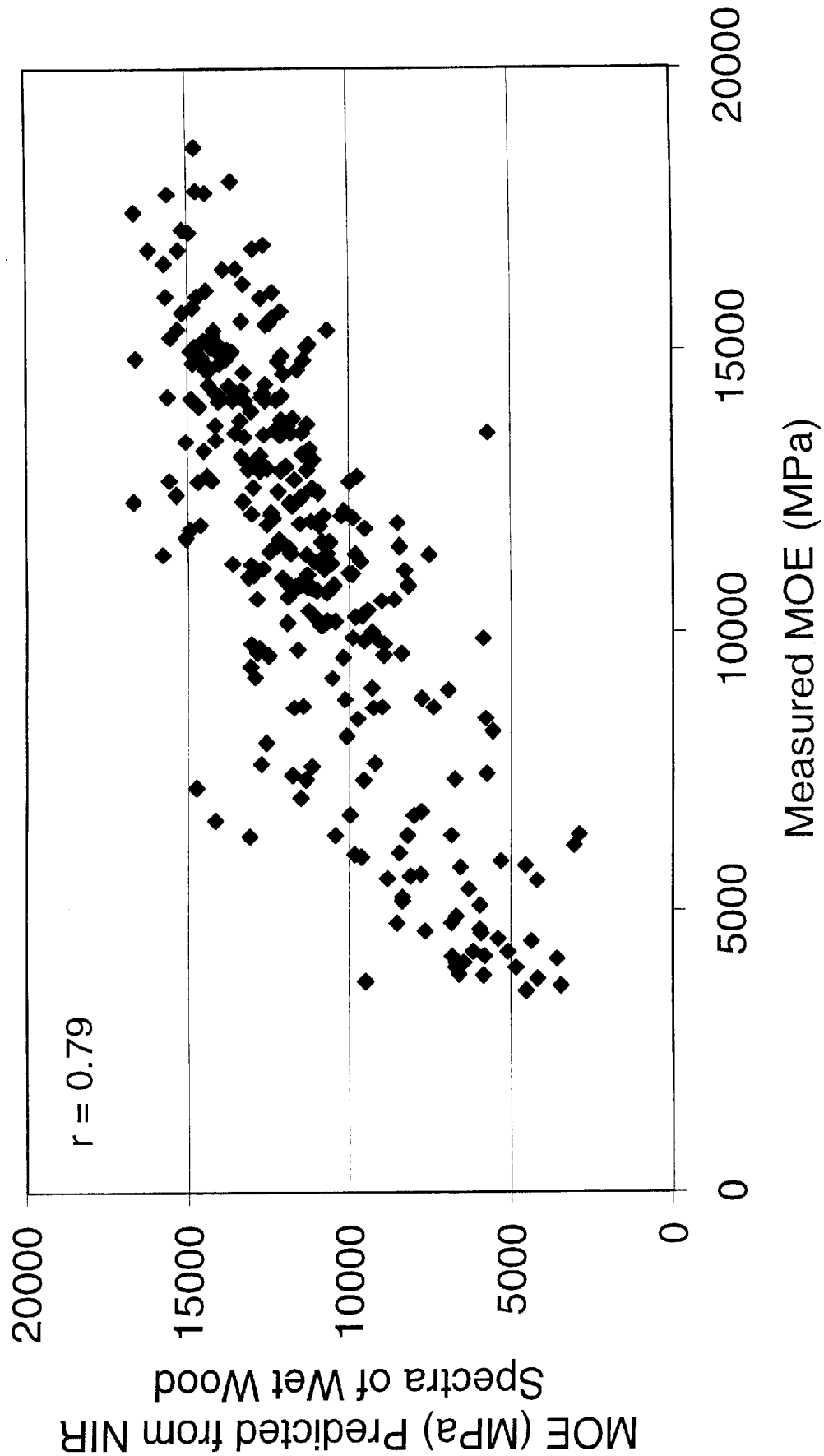
FIG. 19 is a graph of dry stiffness (MOE) of 278 Slash pine samples predicted from the VIS-NIR spectra of wet wood using a 450 nm range (500–950 nm) measured with a diode array detector.

FIG. 19 is a graph of the dry stiffness (MOE) of 278 Slash Pine samples predicted from VIS-NIR spectra of wet wood. This prediction is based on a 450 nm range (500–950 nm) and is measured with a solid-state diode array detector. This plot demonstrates the dramatic improvement in the basic technology since it only uses third and fourth overtones of the actual vibrations of interest and thereby enables use of very fast, inexpensive and lightweight detectors. The use of wavelengths between 500 and 950 nm provides a better correlation than 400–1,150 nm since scatter in the ultraviolet range and short visible region is eliminated.

Figure 20:
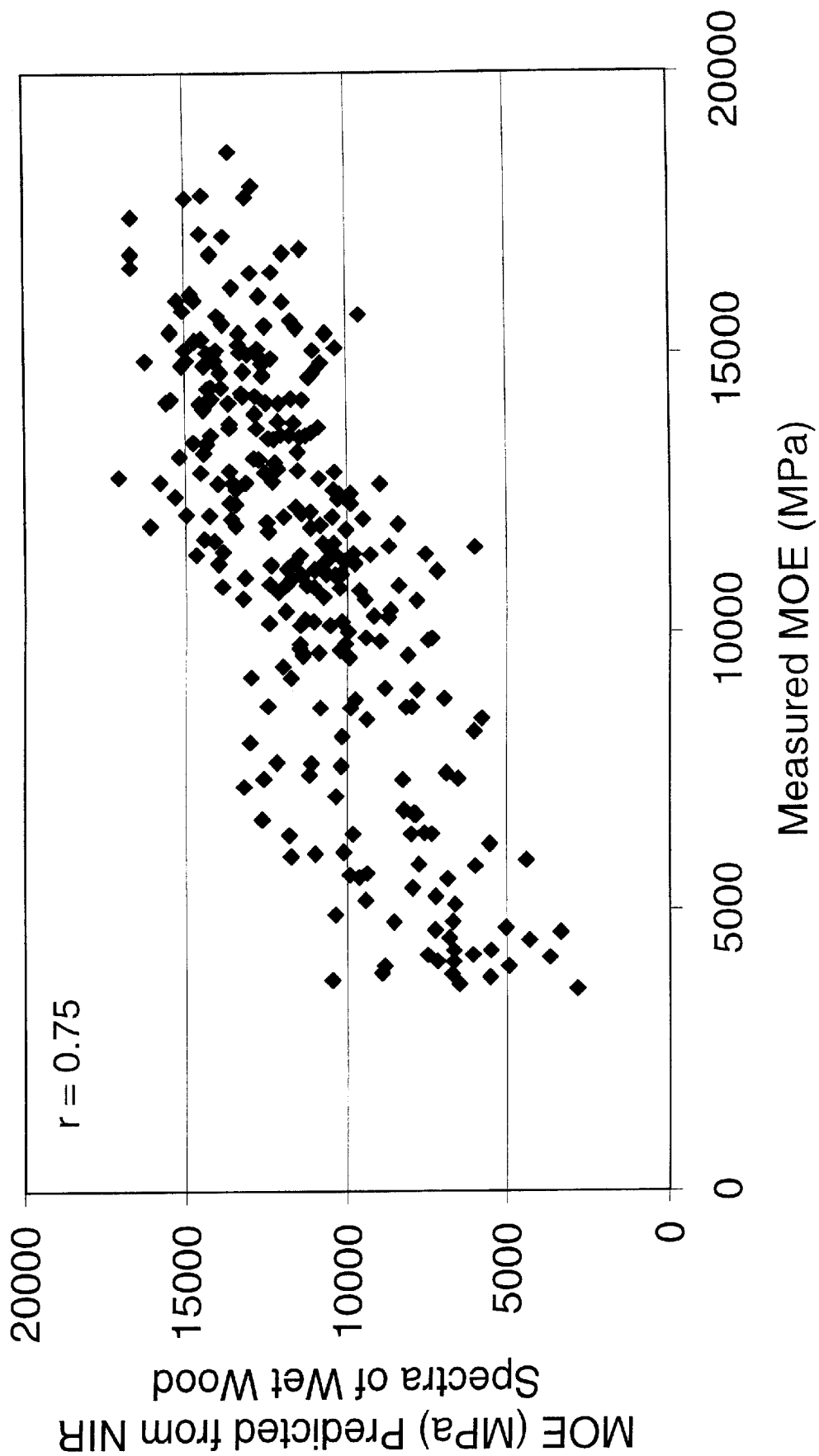
FIG. 20 is a graph of dry stiffness (MOE) of 278 Slash pine samples predicted from the visible spectra of wet wood using a 300 nm range (400–700 nm) measured with a diode array detector.

FIG. 20 is a graph of the dry stiffness (MOE) of 278 Slash Pine samples predicted from visible spectra of wet wood. This prediction is based on a 300 nm range (400–700 nm) and is measured with a solid-state diode array detector. This plot highlights the use of a very narrow spectral range and shows that the scatter between 400–500 nm slightly reduces the strength of the correlation.

Figure 21:
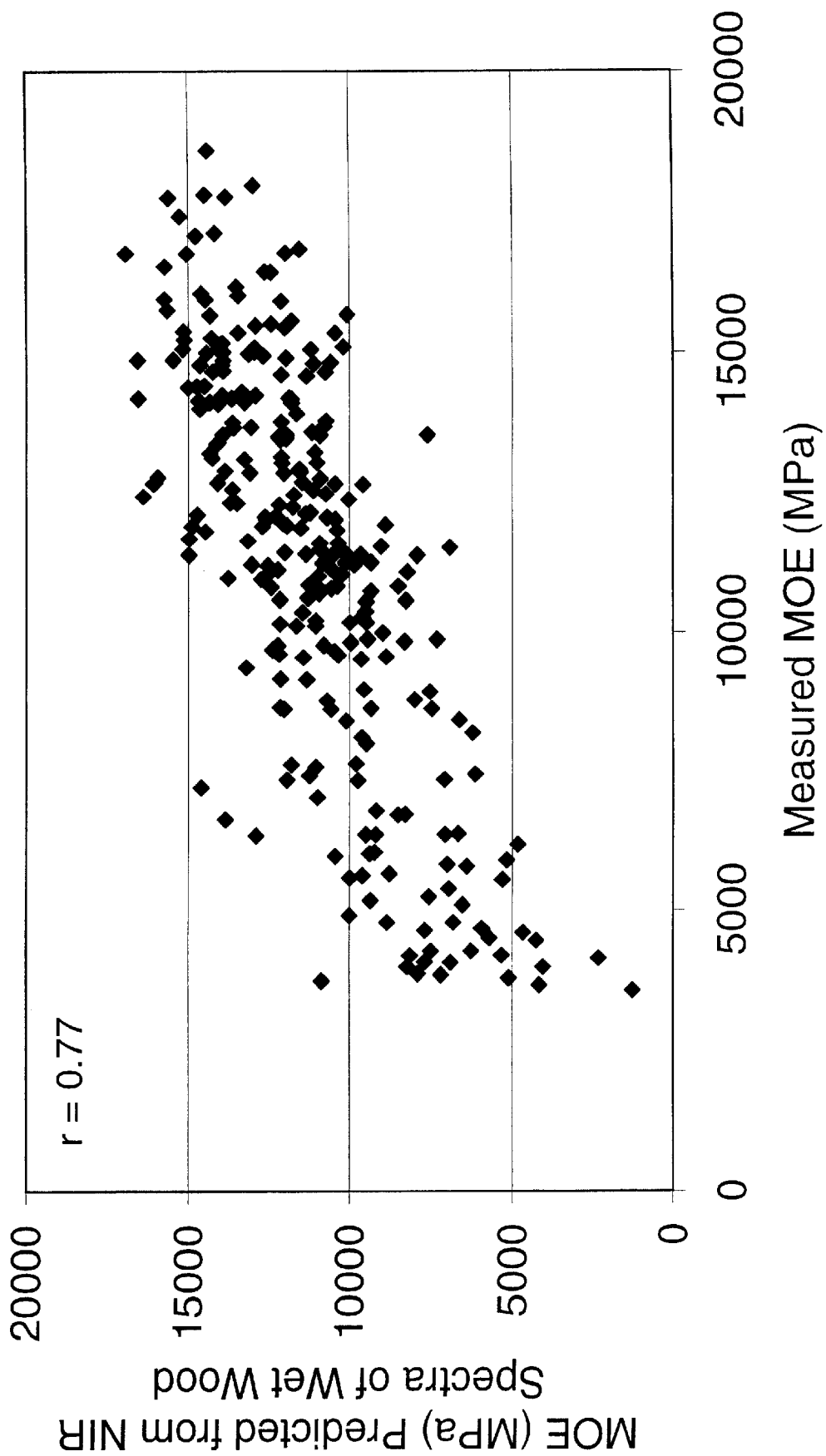
FIG. 21 is a graph of dry stiffness (MOE) of 278 Slash pine samples predicted from the VIS-NIR spectra of wet wood using a 300 nm range (500–800 nm) measured with a diode array detector.

A graph of the the dry stiffness (MOE) of 278 Slash Pine samples is predicted from the VIS-NIR spectra of wet wood is shown in FIG. 21. This prediction is based on a 300 nm range (500–800 nm) and is measured with a solid-state diode array detector. This plot highlights the use of a very narrow spectral range.

Figure 22:
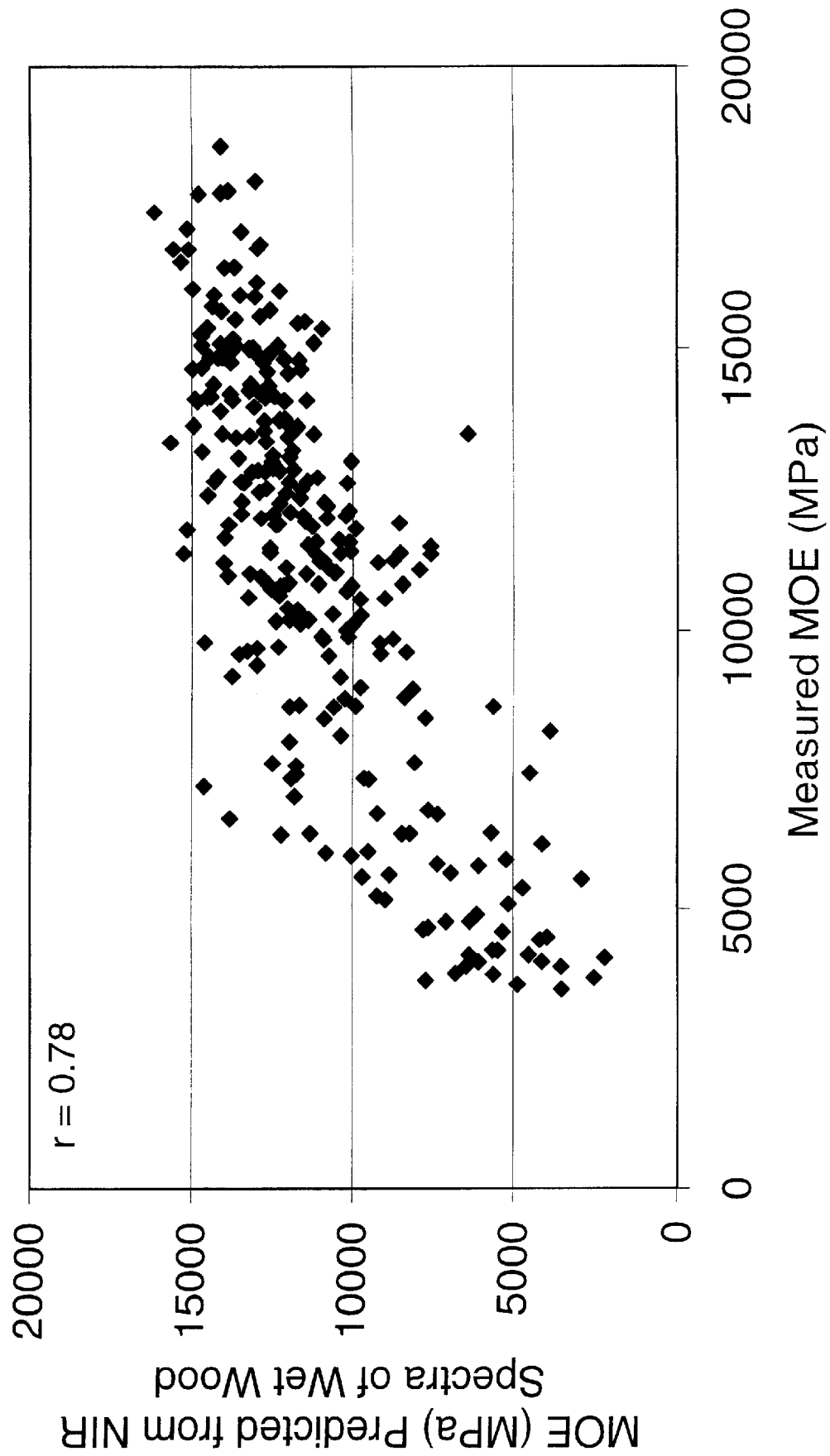
FIG. 22 is a graph of dry stiffness (MOE) of 278 Slash pine samples predicted from the VIS-NIR spectra of wet wood using a 300 nm range (600–900 nm) measured with a diode array detector.

FIG. 22 is a graph of the dry stiffness (MOE) of 278 Slash Pine samples predicted from VIS-NIR spectra of wet wood. The prediction is based on a 300 nm range (600–900 nm) and is measured with a solid-state diode array detector. This plot highlights the use of a very narrow spectral range.

Figure 23:
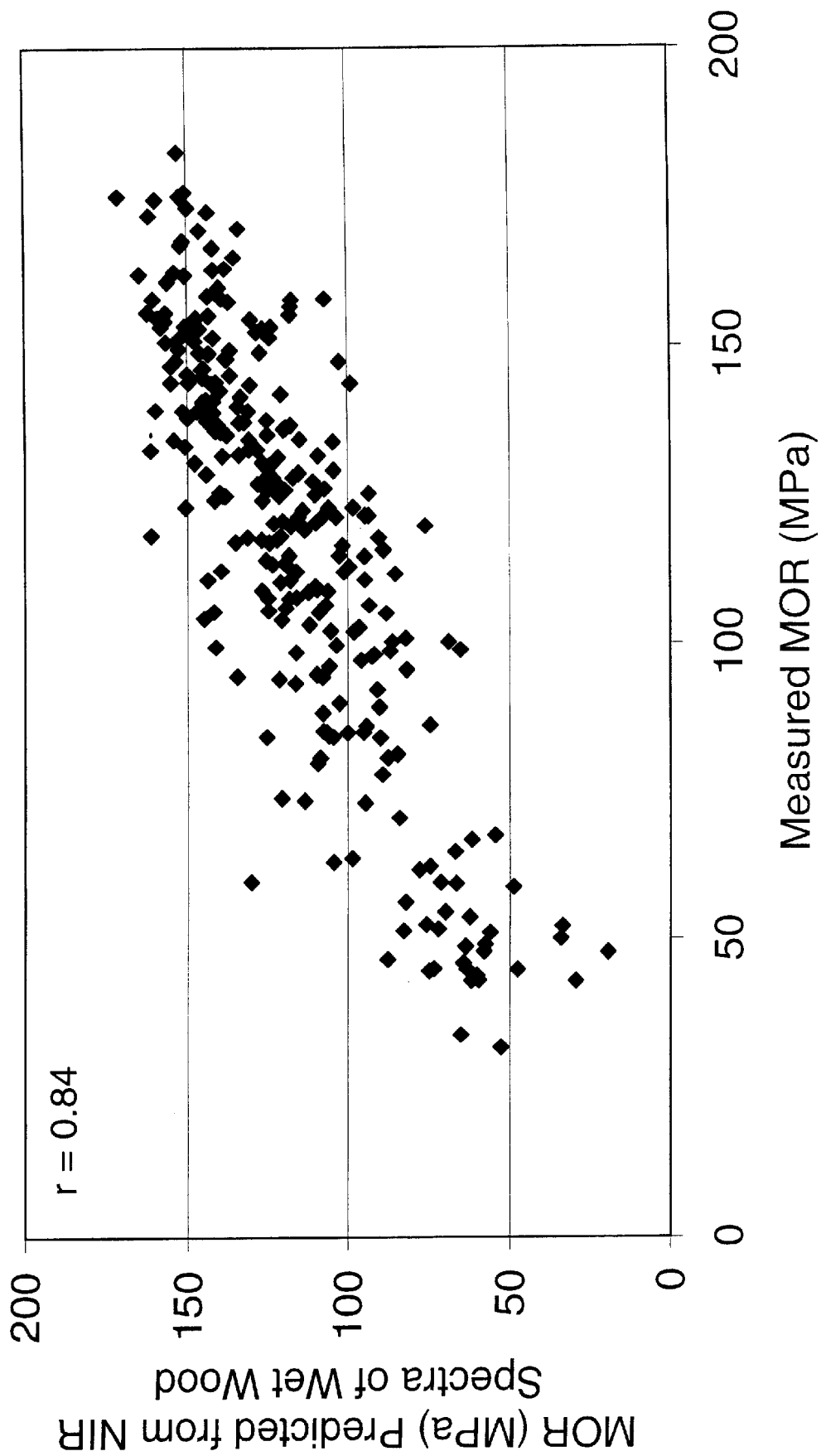
FIG. 23 is a graph of ultimate strength (MOR) of 278 Slash pine samples predicted from the VIS-NIR spectra of wet wood using a 2,150 nm range (350–2,500 nm) individual wavelengths and is the base technology.

A graph of the measured ultimate strength (MOR) of 278 Slash Pine samples is predicted from VIS-NIR spectra of wet wood is shown in FIG. 23. This prediction is based a 2,150 nm range and represents the basic technology.

Figure 24:
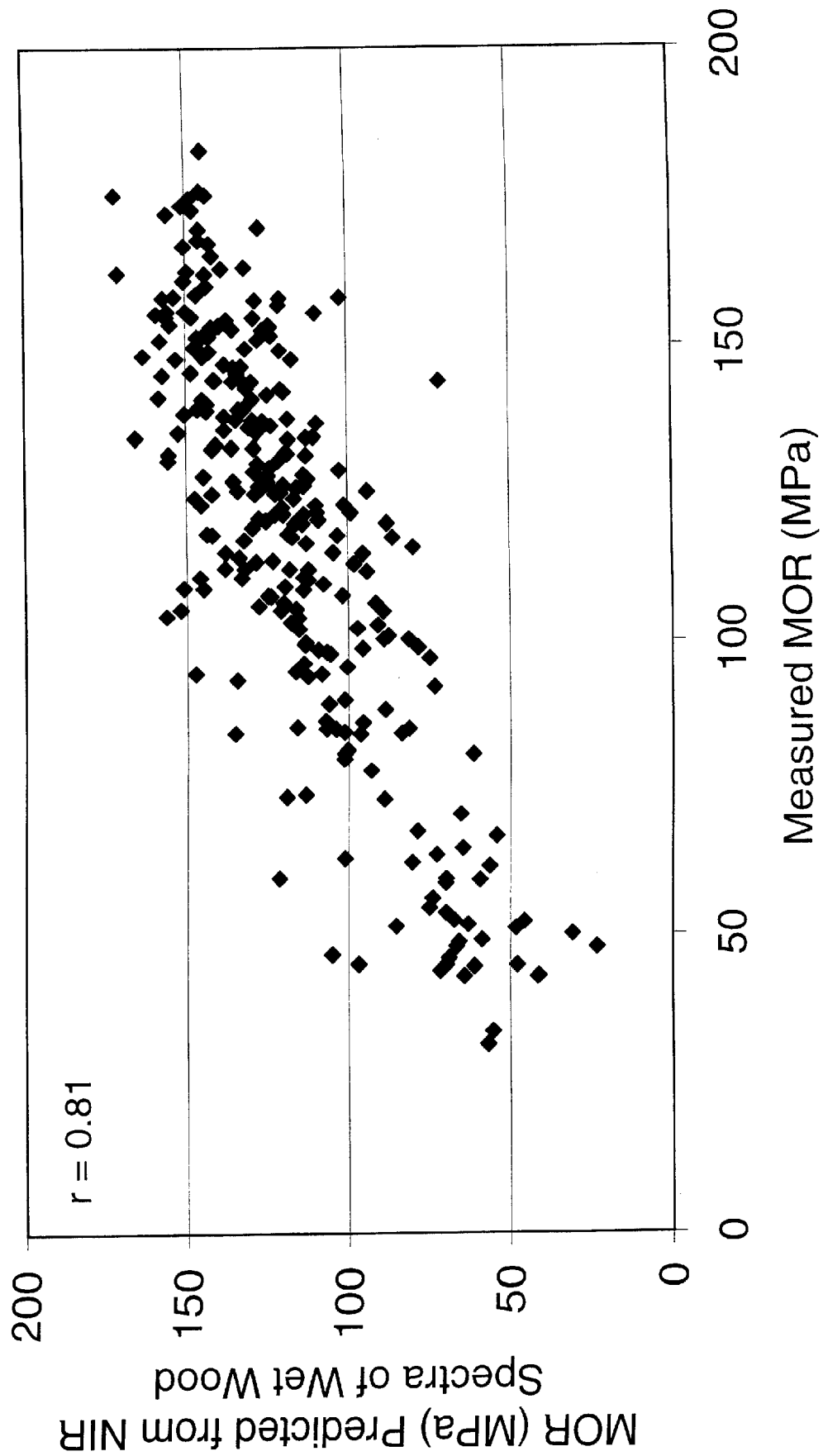
FIG. 24 is a graph of ultimate strength (MOR) of 278 Slash pine samples predicted from the VIS-NIR spectra of wet wood using a 750 nm range (400–1,150 nm) measured with a diode array detector.

FIG. 24 is a graph of the measured ultimate strength (MOR) of 278 Slash Pine samples predicted from VIS-NIR spectra of wet wood. This prediction is based on a 750 nm range (400–1,150 nm) and is measured with a solid-state diode array detector. This plot is a dramatic improvement in the technology since it uses only third and fourth overtones of the actual vibrations of interest and thereby enables use of very fast, inexpensive and lightweight detectors.

Figure 25:
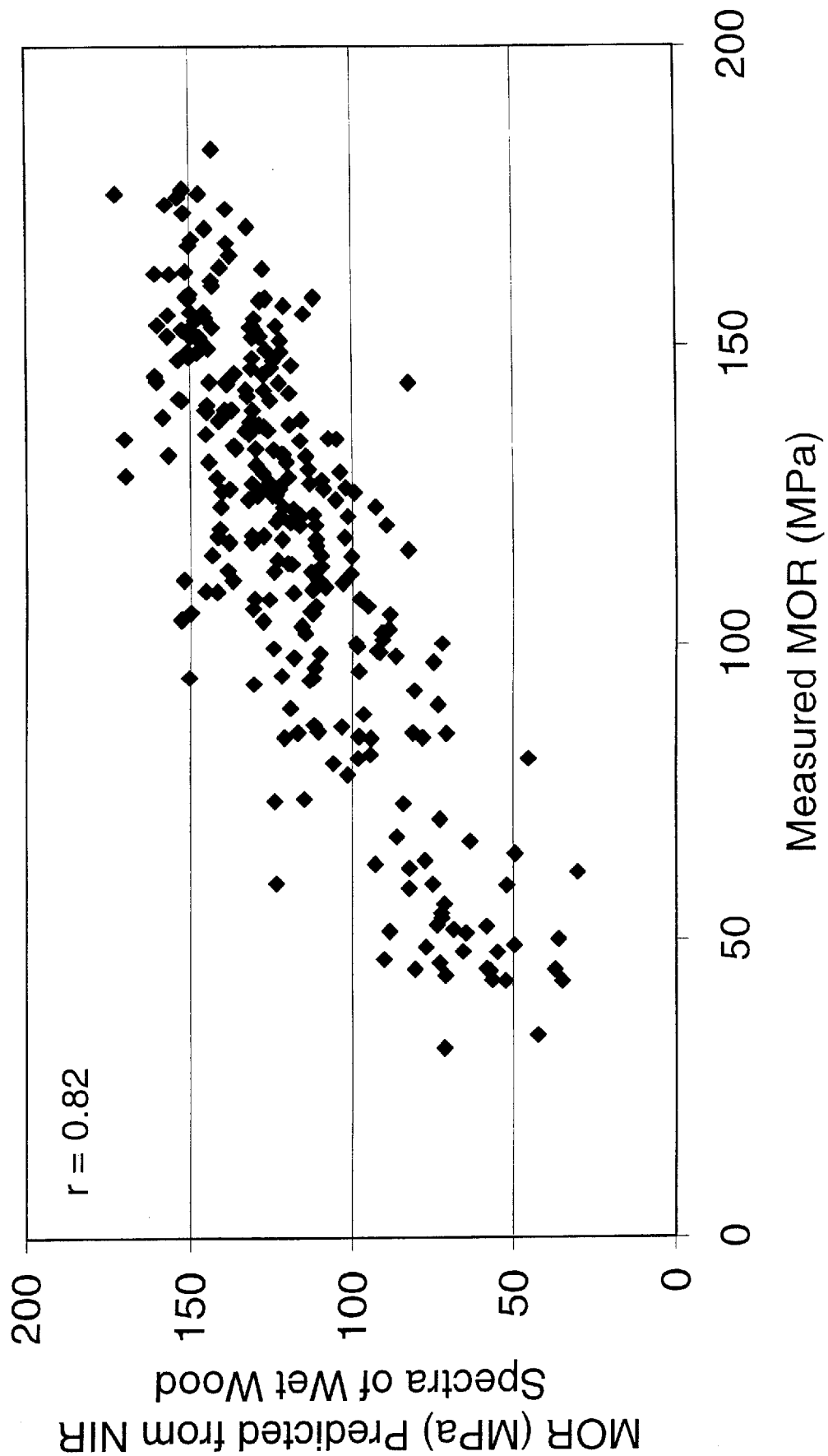
FIG. 25 is a graph of ultimate strength (MOR) of 278 Slash pine samples predicted from the VIS-NIR spectra of wet wood using a 450 nm range (500–950 nm) measured with a diode array detector.

A graph of the measured ultimate strength (MOR) of 278 Slash Pine samples is predicted from VIS-NIR spectra of wet wood is shown in FIG. 25. The prediction is based on only a 450 nm range (500–950 nm) and is measured with a solid-state diode array detector. This plot demonstrates a dramatic improvement over the basic technology since it uses only third and fourth overtones of the actual vibrations of interest and thereby enables the use of very fast, inexpensive and lightweight detectors. The use of wavelengths between 500 and 950 nm provides a better correlation than 400–1,150 nm since scatter in the ultraviolet range and short wavelength visible region is eliminated.

Figure 26:
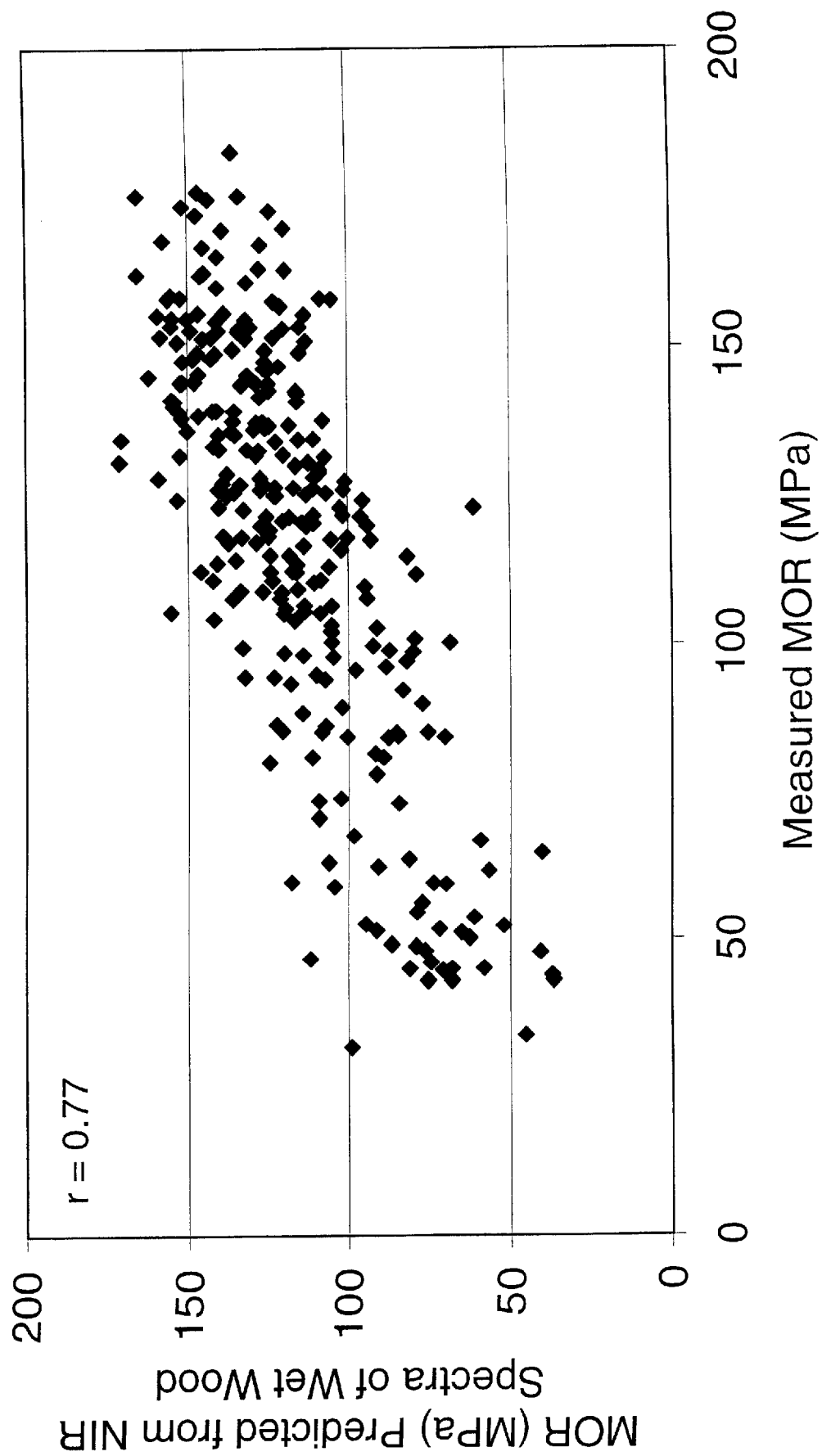
FIG. 26 is a graph of ultimate strength (MOR) of 278 Slash pine samples predicted from the visible spectra of wet wood using a 300 nm range (400–700 nm) measured with a diode array detector.

A graph of the measured ultimate strength (MOR) of 278 Slash Pine samples is predicted from visible spectra of wet wood is shown in FIG. 26. This prediction is based on a 300 nm range (400–700 nm) and is measured with a solid-state diode array detector. This plot highlights the use of a very narrow spectral range, and shows that the scatter between 400–500 nm slightly reduces the strength of the correlation.

Figure 27:
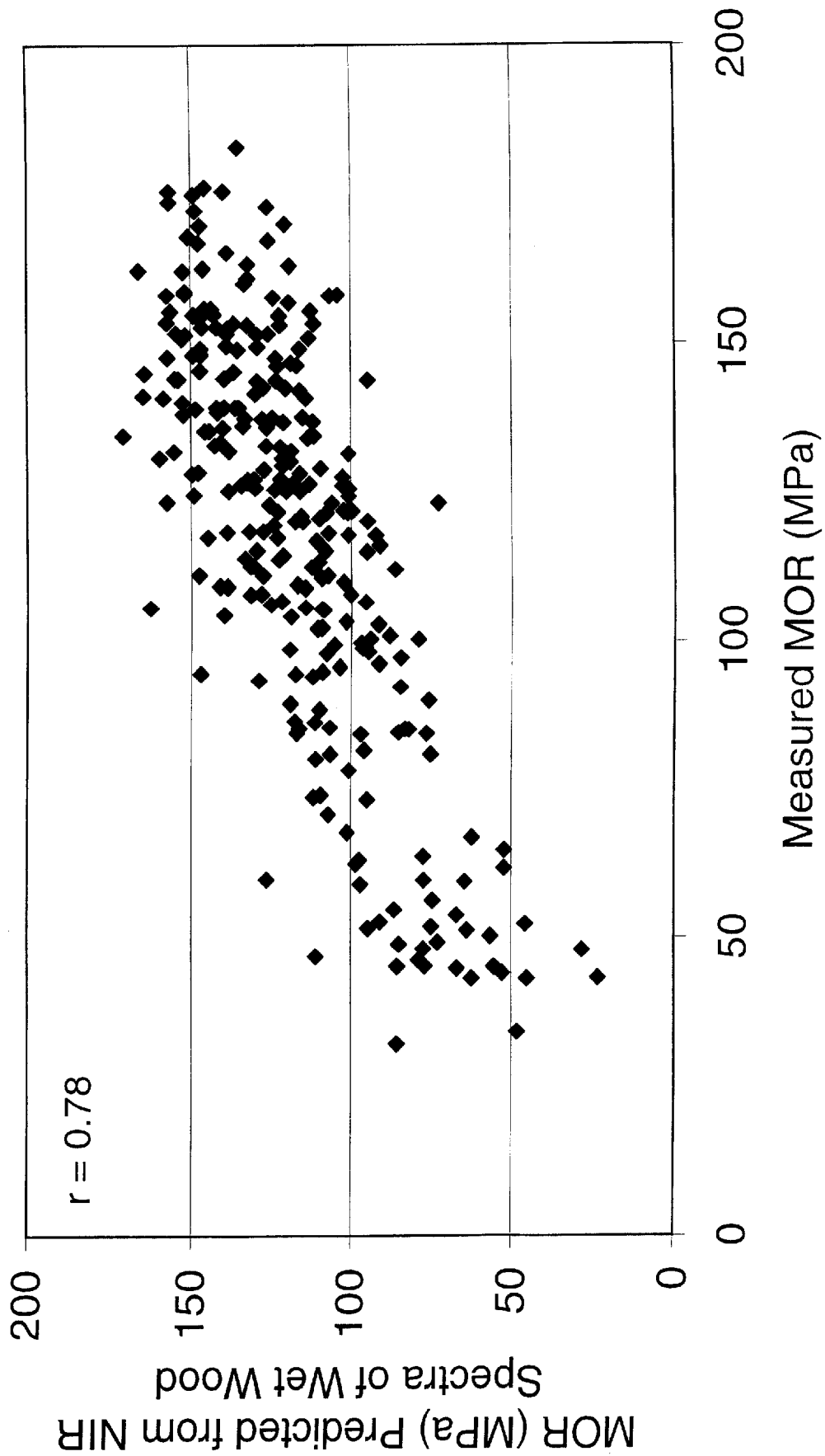
FIG. 27 is a graph of ultimate strength (MOR) of 278 Slash pine samples predicted from the VIS-NIR spectra of wet wood using a 300 nm range (500–800 nm) measured with a diode array detector.

FIG. 27 is a graph of the measured ultimate strength (MOR) of 278 Slash Pine samples predicted from VIS-NIR spectra of wet wood. This prediction is based on a 300 nm range (500–800 nm) and is measured with a solid-state diode array detector. This plot highlights the use of a very narrow spectral range.

Figure 28:
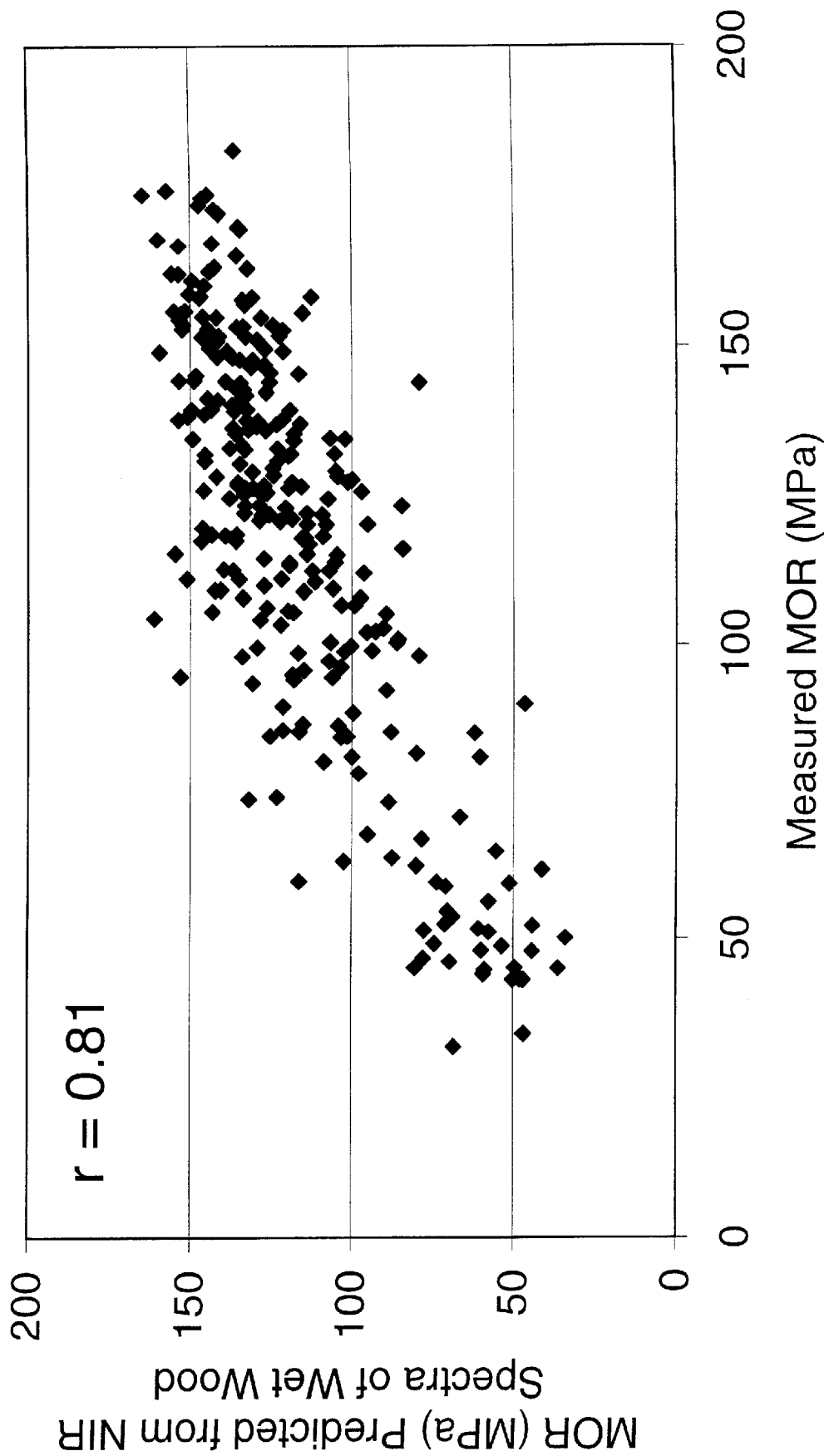
FIG. 28 is a graph of ultimate strength (MOR) of 278 Slash pine samples predicted from the VIS-NIR spectra of wet wood using a 300 nm range (600–900 nm) measured with a diode array detector.

A graph of the measured ultimate strength (MOR) of 278 Slash Pine samples is predicted from VIS-NIR spectra of wet wood is shown in FIG. 28. This prediction is based on a 300 nm range (600–900 nm) and is measured with a solid-state diode array detector. This plot highlights the use of very narrow spectral range.

The correlation coefficients for the PLS models are tabulated in TABLE 1:

TABLE 1

| Wavelengths | Mountain Pine (MOE) | Mountain Pine (MOR) | Slash Pine (MOE) | Slash Pine (MOR) |
| --- | --- | --- | --- | --- |
| 350–2500 | 0.88 | 0.88 | 0.82 | 0.84 |
| 400–1150 | 0.84 | 0.84 | 0.79 | 0.81 |
| 500–950 | 0.89 | 0.85 | 0.79 | 0.82 |
| 400–700 | 0.82 | 0.83 | 0.75 | 0.77 |
| 500–800 | 0.83 | 0.76 | 0.77 | 0.78 |
| 600–900 | 0.84 | 0.83 | 0.78 | 0.81 |

The correlation coefficients and the root mean square error of prediction (RMSEP) for FIGS. 5–28 are shown in TABLE 2.

TABLE 2

| FIGURE NUMBERS | CORRELATION | RMSEP |
| --- | --- | --- |
| FIG. 5 | 0.88 | 125 |
| FIG. 6 | 0.84 | 146 |
| FIG. 7 | 0.89 | 122 |
| FIG. 8 | 0.82 | 154 |
| FIG. 9 | 0.83 | 149 |
| FIG. 10 | 0.84 | 144 |
| FIG. 11 | 0.88 | 1.32 |
| FIG. 12 | 0.84 | 1.58 |
| FIG. 13 | 0.85 | 1.47 |
| FIG. 14 | 0.83 | 1.57 |
| FIG. 15 | 0.76 | 1.82 |
| FIG. 16 | 0.83 | 1.54 |
| FIG. 17 | 0.82 | 2073 |
| FIG. 18 | 0.79 | 2280 |
| FIG. 19 | 0.79 | 2227 |
| FIG. 20 | 0.75 | 2405 |
| FIG. 21 | 0.77 | 2334 |
| FIG. 22 | 0.78 | 2279 |
| FIG. 23 | 0.84 | 18.7 |
| FIG. 24 | 0.81 | 20.6 |
| FIG. 25 | 0.82 | 19.8 |
| FIG. 26 | 0.77 | 21.9 |
| FIG. 27 | 0.78 | 21.6 |
| FIG. 28 | 0.81 | 20.2 |

The improved invention demonstrates the ability to use a reduced range of wavelengths for the determination of dry mechanical strength of green wood using VIS-NIR spectra of the green wood coupled with multivariate analysis.

As can be seen, two sets of samples were analyzed. The first set of samples came from three pine trees cut from a stand in Evergreen, Colo. and are referred to as the "Mountain Pine" sample set.

The second set of samples came from five Slash pine trees cut in Arkansas and is referred to as the "Slash Pine" sample set.

For each set of samples two types of mechanical properties were measured, the MOE and the MOR. The MOE is a measure of the stiffness of the sample and MOR is a measure of the ultimate strength of the sample. In the case of the Mountain Pine sample set the mechanical properties were measured with the load applied to the radial face of the sample. In the case of the Slash pine samples the mechanical properties were also measured with the load applied to the radial face of the samples.

The correlation coefficient is a measure of the "quality" of the prediction made from the VIS-NIR spectra of green wood. The first row in TABLE 1 shows the correlation coefficient for the entire spectral range. The remaining five rows in TABLE 1 show the correlation coefficients obtained for a greatly reduced range of spectral wavelengths. Overall, the data contained in TABLE 1 show that using a greatly reduced range of wavelengths does not reduce the accuracy of the strength of the predictions.

FIGS. 5–16 show the results obtained from the mountain pines sample set that was cut from the stand in Evergreen, Colo. Two logs were cut from each tree and then small bending samples were cut from each log. The VIS-NIR spectrum of each bending sample was collected while the samples were still "green" or wet. The moisture content of these samples was between 20% and 70%. The samples were dried to below 10% moisture content and the MOE and MOR of each sample was measured using an Instron testing machine. Multivariate statistical techniques were then used to calculate correlations between VIS-NIR spectra of the green wood and the measured MOE. The prediction accuracies obtained with models based on wavelengths between 350 and 2500 nm produces prediction correlation coefficients of about 0.88. This correlation coefficient is high enough for this VIS-NIR technique to be useful. Further, the chemical features that drive the correlation do not need to be clearly identified for the correlations to be useful, and while all of the chemical features that drive the correlation have not been assigned, it is clear that these features are related to hydroxyl groups and carbon-hydrogen bonds on the carbohydrates and lignin present in the wood.

FIGS. 6–10 show the predicted accuracy results from MOE obtained from a greatly reduced range of wavelengths. The selection of this subset of wavelengths is the heart of this invention. Reducing the range of wavelengths used for the analysis can be done in a number of ways. However, in this invention the wavelengths were selected based on the spectral range that can be measured with the less expensive, lightweight, durable diode array detectors or optical tunable filter detectors. The good predictions that were observed are unexpected since the model used the visible region of the spectrum that is commonly thought to contain mainly information about the color of a sample. However, it also well known that this region of the spectrum contains chemical information on the hydroxyl groups and carbon-hydrogen bonds on the carbohydrates and lignin present in the wood in the form of third and fourth overtone vibrations. But these higher order overtones are relatively weak and generally overlooked when one is looking for information on the chemical properties of a material. The predictive correlations are derived from the information on chemical composition and the physical structure of wood derived from these overtones.

FIG. 6 shows predictive results based on the spectral range between 400 and 1,150 nm. FIG. 7 shows the results from models using the spectral range is between 500 and 950 nm. The results shown in FIG. 7 are actually slightly better than the results seen for the entire spectral range (FIG. 5). The correlation coefficient for the predictive plot shown in FIG. 7 is also better than the correlation coefficient for the predictive plot shown in FIG. 6.

FIGS. 8–10 shows the results of the analysis for the same set of mountain pine samples but using several smaller regions of the spectra. FIG. 8 shows the results for the range between 400–700 nm that has the poorest correlation coefficient of all of the ranges that were evaluated. However, it should be emphasized that this correlation coefficient is good for a highly variable material like wood and more importantly it allows useful conclusions to be made on the quality and value of the wood sample or tree. FIGS. 9 and 10 show the results of the analysis for the spectral ranges between 500–800 nm and 600–900 nm, respectively.

Taken together these results show that reducing the spectral range from 2,150 wavelengths to 550–300 wavelengths between 400 and 1,150 nm does not reduce the quality of the prediction of MOE Mountain Pine.

FIGS. 11–17 show the same results presented in FIGS. 5–10, however the MOR or strength of the samples is used as the response variable. FIGS. 12 and 13 show the results of the analysis for the spectral ranges of 400–1,150 nm and 500–950 nm, respectively. Again the range between 500–950 nm is slightly better than the broader range. FIGS. 14–16 show the results of the analysis for the three very narrow ranges, 400–700 nm, 500–800 nm, and 600–900 nm, respectively. While the correlation for the range between 500–800 nm is unexpectedly low, the trends in the predictions is similar to those seen with the MOE results.

In total these results show that reducing the spectral range from 2,150 wavelengths to 550 to 300 wavelengths between 400 and 1,150 nm does not reduce the quality of the prediction of MOR mountain pine.

FIGS. 17–28 present results obtained from the Slash Pine sample set. Five Slash Pine trees were cut from a stand in Arkansas and sections were cut every 16 feet. The sections were wrapped in plastics and sent to the National Renewable Energy Laboratory (NREL) by express freight. At NREL the sections were cut longitudinally through the center, and VIS-NIR spectra were of the fresh "green" surface. The moisture content of these samples was between 20% and 70%. Bending samples were then cut from these sections. The bending samples were dried to below 10% moisture content and the MOE and MOR were measured using an Instron testing machine. In this case the force was applied to the radial surface of the samples. Multivariate statistical techniques were used to measure correlations between VIS-NIR spectra of the green wood and the measured MOE and MOR.

The prediction from a model based on wavelengths between 350 nm and 2500 nm is shown in FIG. 17. The correlation coefficient is 0.82. This correlation coefficient is high enough for this technique to be useful. As mentioned, the chemical features that drive the correlations do not need to be clearly identified for the correlations to yield predictive models, and while all of the chemical features that drive the correlation have not been assigned, it is clear that these features are related to hydroxyl groups and carbon-hydrogen bonds on the carbohydrates and lignin present in the wood.

FIGS. 18–22 show the prediction results of models based on a greatly reduced range of wavelengths. The selection of this range of wavelengths is the heart of this invention. Again this set of samples shows that reducing the range of wavelengths used for the analysis can be done in a number of ways. However, in this invention the wavelengths were selected based on the spectral range that can be measured with the less expensive, lightweight, durable diode array detectors. This is the visible region of the spectra, and is commonly thought to only contain information about the color of a sample. However, this region of the spectra also contains chemical information on the hydroxyl groups and carbon-hydrogen bonds on the carbohydrates and lignin present in the wood in the form of third and fourth overtone vibrations. The correlations are derived from the information on chemical composition and the physical structure of wood contained in these overtones.

FIG. 18 shows the predictions for MOE of Slash pine sample obtained by using the spectral range between 400 nm and 1,150 nm. FIG. 19 shows the results when only the spectral range is between 500 nm and 950 nm. FIGS. 20 through 22 shows the results of the analysis for the Slash Pine sample set using several smaller regions of the spectra. FIG. 20 shows the results for the range between 400–700 nm. FIG. 21 shows the results of the analysis for the spectral ranges between 500–800 nm, while FIG. 22 shows the results of the analysis for the spectral range between 600–900 nm.

Taken together these results show that reducing the spectral range from 350 to 2,500 to between 400 and 1,150 nm, does not have a negative impact of the quality of the prediction of the MOE of Slash Pine.

FIGS. 23–28 show the same results that were presented in FIGS. 17–22, but the Slash Pine MOR or strength was used as the response variable in the PLS models. FIG. 23 shows the correlation between the measured MOR and MOR predicted from models using the entire spectral range, 350–2500 nm. FIGS. 24–25 show the results of the models for the spectral ranges of 400–1,150 nm and 500–950, respectively. As was seen before, the range between 500–950 nm is slightly better than the broader range. FIGS. 26–28 show the results of the analysis for three very narrow ranges, 400–700 nm, 500–800 nm, 600–900 nm, respectively. Again the trends in the predictions are similar for those seen with the Slash Pine MOE results, and both the MOE and MOR results derived from the Mountain Pine sample set. Taken together, these results show that reducing the spectral range from 2,150 wavelengths to 550 or 300 wavelengths, and between 400 and 1,150 nm, does not have a substantial negative impact of the quality of the prediction of the MOR of Slash Pine.

Over a given region of the VIS-NIR spectra there is a second way to reduce the number of data points that are used in the calibration and predictive models described in this invention. This second method involves averaging the spectral data. Averaging the spectral data has several advantages including reducing the computational time for the data processing and analysis, decreasing the cost of the computer used for the data analysis and increasing the signal to noise ratio in the spectral data.

TABLE 3 shows the results of averaging the spectral data over several different wavelength intervals. All of the spectra were collected between 400 and 1,150 nm. It is clear that averaging the spectra over different intervals, up to 32 nm does not have a substantial negative impact on the quality of the correlations. This analysis shows that with the proper data processing and handling the mechanical properties of green wood can be successfully predicted with 20 to 30 individual data points.

TABLE 3

| Wavelength Intervals | Mountain Pine (MOE) | Mountain Pine (MOR) | Slash Pine (MOE) | Slash Pine (MOR) |
| --- | --- | --- | --- | --- |
| 1 nm (base case) | 0.85 | 0.84 | 0.79 | 0.81 |
| 2 nm | 0.85 | 0.84 | 0.79 | 0.81 |
| 4 nm | 0.85 | 0.84 | 0.78 | 0.81 |
| 8 nm | 0.87 | 0.84 | 0.79 | 0.81 |
| 16 nm | 0.84 | 0.85 | 0.80 | 0.82 |
| 32 nm | 0.81 | 0.82 | 0.79 | 0.81 |
| 64 nm | 0.79 | 0.78 | 0.75 | 0.79 |

It is important to note that the spectra and the bending load was applied to different wood surfaces, radial, and tangential, and the results from both surfaces are useful, and while the strength of the correlation coefficient was not significantly decreased as a result of decreasing the spectral window, the ease, speed, reliability and cost of the spectrometer that can be used to collect the spectra was greatly reduced. This is unexpected since the spectral range that has been selected for this analysis is the visible region of the spectra that is thought to only contain information on the color of the sample. Instead, the MVA analysis has been able to extract information from the third and fourth overtone of hydroxyl and carbon-hydrogen stretching vibrations that are related to the mechanical properties of the wood substrate. These overtones can be identified even though the wood is wet, above 20% moisture content and the raw spectra are dominated by the vibrations associated with free water, which has nothing to do with the strength of the dry wood.

Figure 29:
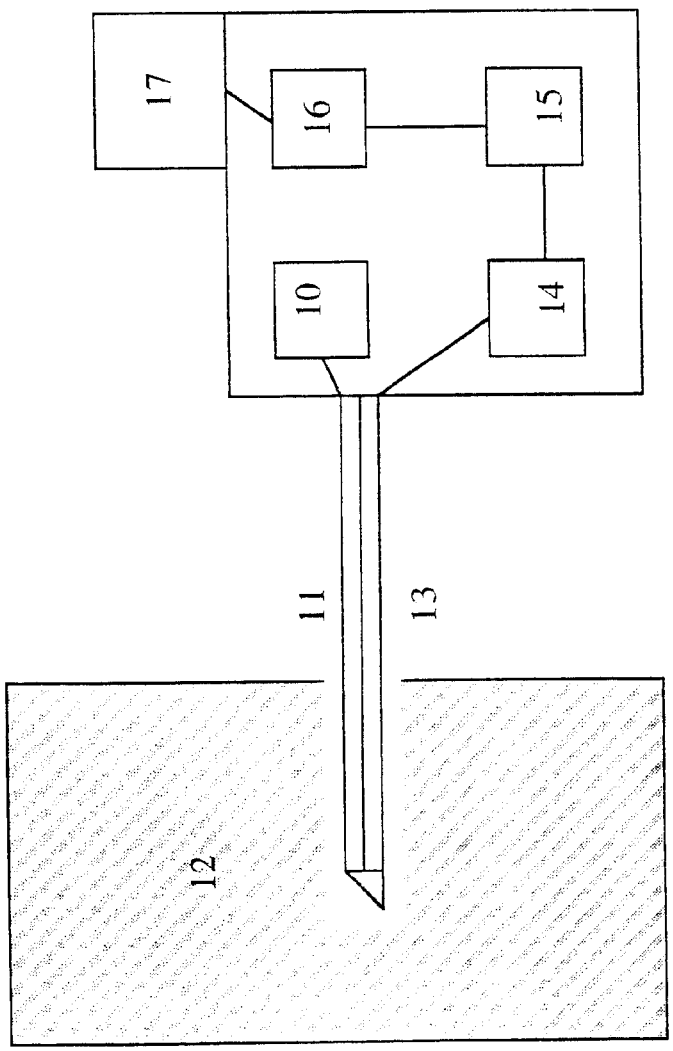
FIG. 29 is a depiction of the invention components for measuring the mechanical properties of a standing tree or log.

A preferred embodiment of the invention used to measure the mechanical properties of a standing tree or log is shown in FIG. 29. The source 10 is transferred through an optical fiber or group of optical fibers 11 to the sample 12. The source of the illumination can be a common quartz-envelope tungsten-halogen incandescent light, or similar source that delivers a broad spectrum of energy in the range between about 400 nm to about 1,150 nm. The source can also be a light emitting diode, a laser with a narrow wavelength or the output of an acoustical optic tunable filter. The energy can be delivered to the sample by illuminating the sample at a distance of a few inches to several feet, or through an optical fiber or set of optical fibers that are in close contact, or direct contact with the wood sample. When polychromatic light is used for illumination then polychromatic light is reflected back from the sample and passes through an optical fiber or set of optical fibers 13 to the monochromator 14.

The preferred spectrometer uses a reduced range of wavelengths and is designed without moving components. The surface of the tree or log to be illuminated will depend on the nature of the sample and may be either an internal surface of a hole drilled into the tree or log, or a surface exposed by removing the bark of the tree or log. In either case it is preferred to have the illumination on the sides of the wood fibers, generally referred to as the radial or tangential face of the wood in the tree or log. Measuring the end of a cut log is also a method of the invention.

In the preferred embodiment the monochromator 14 includes a fixed diffraction grating and detector based on a photodiode collector or a photomultiplier comprised of a number of photodiodes. The reflected polychromatic radiation is transmitted to the diffraction grating and separated into monochromatic energy. The monochromator may also be an acoustical optic tunable filter (AOTF), which is based on the combination of a birefringent crystal and a field oscillating at a specified frequency, (which is commonly in the radio frequency range). Changes in the frequency of the oscillating field or the composition of the birefringent crystal can change wavelength of the energy that passes through the acoustical optic tunable filter. Both the fixed diffraction grating monochromator and AOTF are small, lightweight, inexpensive, have no moving parts, and have low power requirements.

A photodiode collector or a photomultiplier is an extremely sensitive and rapid detector 15. Electric current output of this detecting device is directly proportional to the rate at which photons strike a radiation-sensitive anode. If the photons have been monochromatized, the detector provides a spectrum with useful information of the chemical or mechanical properties of the sample. This current is collected and processed by various electronic means, and is amplified to give an electrical signal which is proportional to the amount of a component or feature present in the sample. Photoelectric detection is best suited to trace determinations because of its high sensitivity. Arrays of photomultiplier tubes have been constructed for simultaneous observation of hundreds or thousands of wavelengths.

A computer 16 is used to collect data on the intensities and wavelengths of the reflected radiation at the detector. This data can be displayed on a cathode-ray tube, recording instrument, or signal means such as a diode, lamp, or current 17. In the computer 16 the data may be converted to a form useful for further data processing, in particular data processing techniques that involve multivariate statistical techniques. Generally the output will be processed using a calibration set and a PLS model or some other similar technique, so that the output is a measurement of mechanical or physical features of the sample, rather than the VIS-NIR spectrum. However, the output is based on the VIS-NIR spectrum measured with the photodetector 15.

Figure 30:
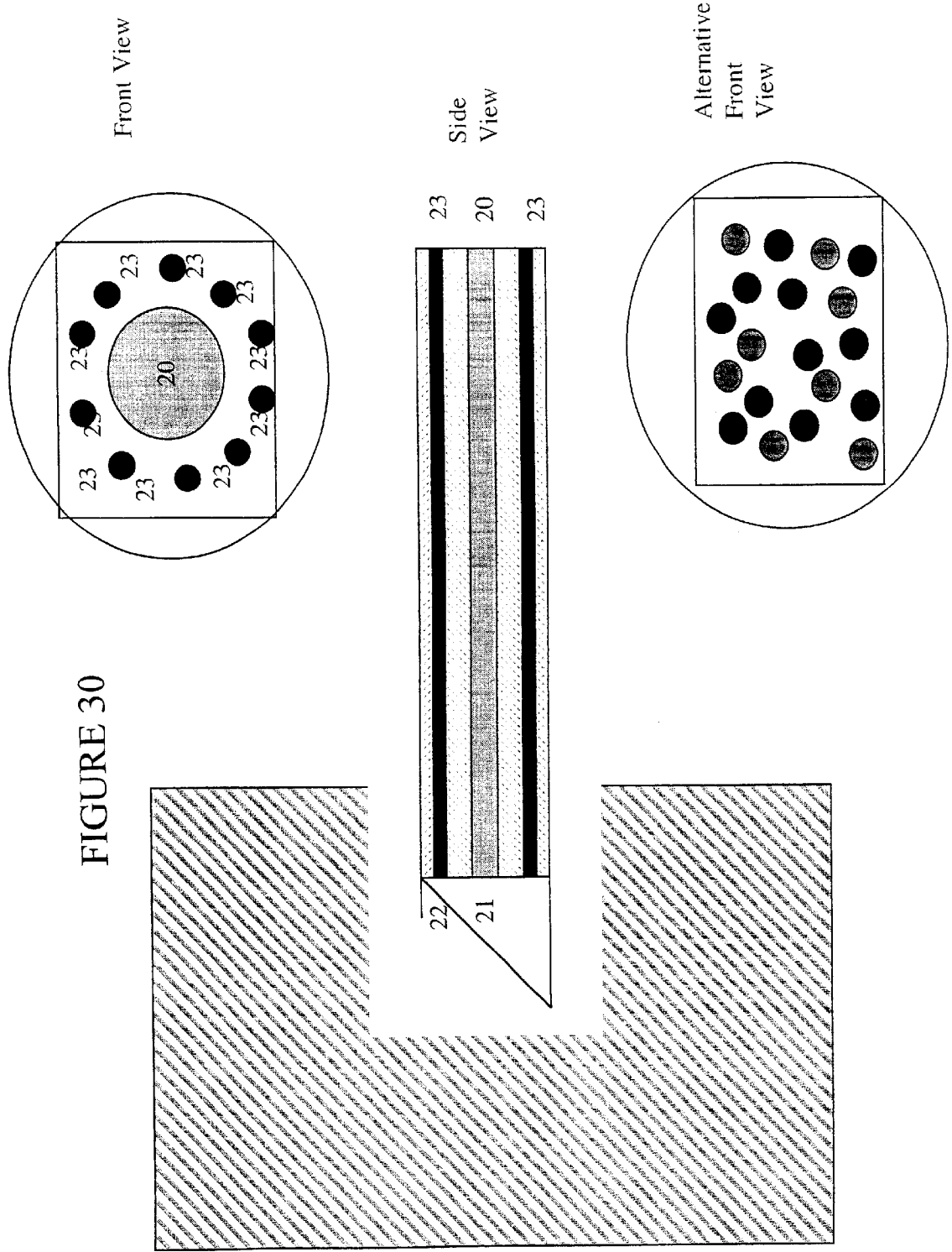
FIG. 30 is a schematic showing the design of a probe used for measuring the mechanical properties of a tree or log using a hole drilled into a tree.

FIG. 30 shows a schematic for the design of the probe used for measuring the mechanical properties of a tree or log using a hole drilled into the tree. The source light is carried into the hole in the tree or log by an optical fiber or group of optical fibers 20. The illumination fibers may be randomly spaced in the fiber optic element or concentric around the observation fiber or fibers. A prism 21 is used to direct a significant portion of the illumination onto the wood fibers, preferably the radial face or tangential face of the wood fibers. The angle 22 on the face of the prism 21 may vary between about 30 to about 60 degrees, although an angle of 45 degrees is preferred. The source illumination interacts with the wood substrate and a portion is reflected back onto the prism 21 and is passed on to a second optical fiber or set of optical fibers 23. Then the reflected illumination is carried back into the spectrometer and processed as shown in FIG. 29

The present invention utilizes an improved VIS-NIR spectrophotometer apparatus, particularly suited for determining the physical properties of wood. For the purpose of the present invention, spectral information refers to light having wavelengths in the visible (400 nm to about 800 nm), and near-infrared (800 nm to about 2,500 nm) regions. Spectral images, for purpose of the present invention, are the particular spectra or segments of spectra, often described as the relationship of optical wavelength, frequency, or the like (x-axis) and absorbance, reflectance, transmittance, light intensity, or the like (y-axis), corresponding to a particular spectrophotometric analysis.

The optical features of the VIS-NIR range, a range particularly suited for the analysis of the physical properties of wood, are generally combinations and overtones of vibrational modes found in the infrared region (2,500 nm to about 25,000 nm). Generally, asymmetric bonds having dipole moments create detectable and distinguishable features in the infrared region. In particular, combinations and overtones associated with the fundamental infrared absorbance associated with the bonds H—X, where H is hydrogen and X is carbon, nitrogen, or oxygen, give particularly intense features. Overtone bands of the H—O, H—C stretching mode and overtones of combination bands of H—O and C—H stretching and bending modes are found in the region between 400 nm and 1,150 nm. Each set of overtone and combination bands contain similar information.

Since some bands in the VIS-NIR range contain similar information, a narrower frequency range can be utilized to obtain accurate determinations of physical and mechanical properties. Generally, any overtone band, combination band, or combination of overtone and combination bands can be utilized; however, a particular range is generally preferred depending on the system under analysis. For example, for the analysis of wood or lignocellulosics, the wavelength range of between about 920 nm and about 960 nm that can be attributed to the second overtone of hydrogen-oxygen bonds are particularly useful. The wavelength range between 850 nm to about 1000 nm and spanning the third carbon-hydrogen stretching overtone is also useful. The wavelengths regions of between about 720 run and about 750 nm that can be assigned to the third overtone of hydrogen-oxygen bands and are also useful for prediction of mechanical properties.

VIS-NIR analysis is commonly used to determine the chemical composition complex mixtures from their spectral information. While it is not obvious, physical and mechanical properties can also be quantitatively correlated to spectral information where the property is related to the composition or molecular features that are embodied in the spectra.

The spectral correlations developed for use in spectrophotometric devices in accordance with the present invention are generally built utilizing most or much of the spectrum of the sample although suitable correlations can also be developed using the absorbances measured at a few select wavelengths. Although a spectrum can consist of several hundred intensities measured at different wavelengths, many of these data points are highly interdependent, or colinear. Multivariate regression can be used to simplify the spectrum into latent variables which describe the independent variations in the spectra for a set of samples. The scores or relative magnitudes of the latent variables in the spectrum change as the properties of the sample change. The number of latent variables necessary to accurately model a system generally depends on the system being analyzed. Generally, the properties can be modeled using less than 15 latent variables, frequently less than 10 latent variables, and often less than 8 latent variables. The number of latent variables minimally necessary to predict mechanical properties can be estimated using splitting techniques, by plots of variance fit using successive numbers of latent variables, or other forms of statistical analysis.

While the present invention has been illustrated and described with reference to particular methods for determining dry mechanical strength for green wood, it will be apparent that modifications can be made therein within the scope of the present invention without departing from the inventive concept, which is defined by the appended claims.

We claim:

1. In a method for determining the dry mechanical strength for a green wood, the improvement comprising:
   (a) illuminating a surface of the wood to be determined with a reduced range of wavelengths in the VIS-NIR spectra, said wood having a green moisture content;
   (b) analyzing the surface of said green wood using a spectrometric method, the method generating a first spectral data of a reduced range of wavelengths in VIS-NIR spectra; and
   (c) using a multivariate analysis to predict the mechanical strength of green wood when dry by comparing said first spectral data with a calibration model, said calibration model comprising a second spectrometric method of spectral data of a reduced range of wavelengths in VIS-NIR spectra obtained from a reference wood having a green moisture content, the second spectral data being correlated with a known mechanical strength analytical result obtained from said reference wood when dried and having a dry moisture content.

2. The process of claim 1 wherein said green wood is a soft or hard wood.

3. The process of claim 1 wherein said green wood has a moisture content greater than 15% weight.

4. The process of claim 1 wherein said green wood has a moisture content greater than 20% by weight.

5. The process of claim 1 wherein said dry moisture content is less than 10% by weight.

6. The process of claim 1 wherein said dry moisture content is less than 15% by weight.

7. The process of claim 1 wherein said reference wood moisture content is in the range of 15% to 100% by weight.

8. The process of claim 1 wherein said mechanical strength is modulus of elasticity or modulus of rupture.

9. The process of claim 1 wherein said multivariate analysis is selected from Projection to Latent Structures (PLS), Principal Component Analysis (PCA), Partial Least Squares Regression (PLSR), Principal Component Regression (PCR), and Multilinear Regression Analysis (MLR).

10. The process of claim 1 wherein said green wood is a green feedstock for use in a process having a dry lumber, wood chip, veneer, or flake product.

11. The process of claim 10 further comprising outputting the mechanical strength and using the output in sorting the feedstock relative to the product.

12. The process of claim 10 further comprising outputting the mechanical strength and using the output in sorting the product relative to the feedstock.

13. The method of claim 1 wherein said reduced range of wavelengths in said VIS-NIR spectra is between about 300 to about 550 wavelengths in between the range of from 400 to about 1,150 nm comprising of a number of individual data points.

14. The method of claim 13 wherein said green wood is selected from hard wood or a soft wood.

15. The method of claim 14 wherein said reduced range of wavelengths is about 750 individual wavelengths between a range of about 400 to about 1,150 nm.

16. The method of claim 14 wherein said reduced range of wavelengths is about 450 individual wavelengths between a range of about 500 to about 950 mn.

17. The method of claim 14 wherein said reduced range of wavelengths is about 300 individual wavelengths between a range of about 400 to about 700 nm.

18. The method of claim 14 wherein said reduced range of wavelengths is about 300 individual wavelengths between a range of about 500 to about 800 nm.

19. The method of claim 14 wherein said reduced range of wavelengths is about 300 individual wavelengths between a range of about 600 to about 900 nm.

20. The method of claim 13 wherein said number of individual data points can be further reduced by averaging spectral values over several nanometers, said average is between 2–64 nm.

21. The method of claim 20 wherein said number averaged spectral range is between 2–16nm.

22. A method for determining the dry mechanical strength of green timber of a standing tree, comprising:
   (a) illuminating a surface of the standing tree, said tree having a green moisture content and analyzing the surface of said tree using a spectrometric method, the method includes a portable instrument means, generating a first spectral data; and
   (b) using a multivariate model to predict the mechanical strength of said tree when dry by comparing the first spectral data with a calibration model, said calibration model comprising a second spectrometric method of spectral data obtained from a reference wood having a green moisture content, the second spectral data being correlated with a known mechanical strength analytical result obtained from said reference wood when dried and having a dry moisture content.

23. The method of claim 22 further comprising outputting the mechanical strength and using the output to identify timber for thinning or harvesting.

24. The process of claim 22 wherein said surface is a hole or cut in said timber and said portable instrument means include a fiber optic probe and a prism assembly, wherein said assembly projects a beam of light at an angle of about 90° incident to a fibrous alignment of said timber.

25. The process of claim 22 wherein said multivariate analysis is selected from Projection to Latent Structures (PLS), Principal Component Analysis (PCA), Partial Least Square Regression (PLSR), Principal Component Regression (PCR), and Multilinear Regression Analysis (MLR).

26. In a method for determining the dry mechanical strength of green timber of a standing tree, the improvement comprising:
(a) illuminating a surface of the standing tree with a reduced range of wavelengths in the VIS-NIR spectra, said tree having a green moisture content and analyzing the surface of said tree using a spectrometric method, the method includes a portable instrument means having rapid spectral acquisition times less than 3 seconds, generating a first spectral data of a reduced range of wavelengths in the VIS-NIR spectra; and
(b) using a multivariate analysis to predict the mechanical strength of said tree when dry by comparing said first spectral data with a calibration model, said calibration model comprising a second spectrometric method of spectral data of a reduced range of wavelengths in the VIS-NIR obtained from a reference wood having a green moisture content, the second spectral data being correlated with a known mechanical strength analytical result obtained from said reference wood when dried and having a dry moisture content.

27. The method of claim 26 further comprising outputting the mechanical strength of toughness, compression strength, buckling strength, tensional strength and stiffness, shear strength, and screw or nail withdrawal load, and using the output to identify timber for thinning or harvesting.

28. The process of claim 26 wherein said surface is a hole or cut in said timber and said portable instrument means include a fiber optic probe and a prism assembly, wherein said assembly projects a beam of light at an angle of about 90° incident to a fibrous alignment of said timber.

29. The process of claim 26 wherein said portable instrument means have rapid acquisition times of between about 10 microseconds to about 1 second.

30. The process of claim 29 wherein said portable instrument means of said VIS-NIR system comprises inclusion of a solid-state diode array detector.

31. An apparatus for determining the dry mechanical strength of green wood comprising:
(a) source means for illuminating a green wood sample with incident radiation containing a spectral region of energy with a reduced range of wavelengths measurable with detectors having rapid spectral acquisition times of less than 3 seconds in VIS-NIR spectrum of from about 400 nm to about 1,1150;
(b) means for transferring said incident radiation from said source means to a green wood sample;
(c) return means for carrying reflected radiation from said sample to collecting reflected radiation means;
(d) rapid spectral acquisition time photo-detector means sensitive to collected radiation of said reduced range of wavelengths in less than 3 seconds;
(e) computer means to collect intensities and reduced wavelengths of said reflected radiation at said detector means to generate a first spectral data; and
(f) multivariate analysis means to predict the mechanical strength of green wood when dry by comparing said first spectral data with a calibration model, said calibration model comprising a second spectrometric method of spectral data obtained from a reference wood having a green moisture content, the second spectral data being correlated with a known mechanical strength analytical result obtained from said reference wood when dried and having a dry moisture content.

32. The apparatus of claim 31 wherein said means for transferring incident radiation and said means for carrying reflected radiation is an optical fiber or set of optical fibers.

33. The apparatus of claim 32 wherein said collecting reflected radiation means is a monochromator.

34. The apparatus of claim 32 wherein said means for transferring said incident radiation and said means for carrying said reflected radiation comprises prism means disposed about said optical fiber or set of optical fibers in proximity to said green wood sample to direct a portion of said radiation through transferring optical fibers onto wood fibers of said sample and to collect a portion of said reflected radiation through collecting optical fibers.

* * * * *